(12) United States Patent
Ducoux et al.

(10) Patent No.: US 8,486,971 B2
(45) Date of Patent: Jul. 16, 2013

(54) DERIVATIVES OF 3-ALKOXY-4,5-DIARYLTHIOPHENE-2-CARBOXAMIDE, PREPARATION THEREOF, AND THERAPEUTIC USE THEREOF

(75) Inventors: Jean-Philippe Ducoux, Paris (FR); Murielle Rinaldi-Carmona, Paris (FR); Arnaud Rouquette, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/258,933

(22) PCT Filed: Mar. 25, 2010

(86) PCT No.: PCT/FR2010/050551
§ 371 (c)(1),
(2), (4) Date: Jan. 5, 2012

(87) PCT Pub. No.: WO2010/109150
PCT Pub. Date: Sep. 30, 2010

(65) Prior Publication Data
US 2012/0115906 A1   May 10, 2012

(30) Foreign Application Priority Data

Mar. 27, 2009 (FR) .................................. 09 01465

(51) Int. Cl.
*A61K 31/445* (2006.01)
*C07D 409/02* (2006.01)

(52) U.S. Cl.
USPC ........... 514/326; 546/184; 546/207; 546/212; 514/315; 514/317

(58) Field of Classification Search
USPC .................. 546/184, 192, 207, 212; 514/315, 514/317, 326
See application file for complete search history.

(56) References Cited

U.S. PATENT DOCUMENTS 7,462,631 B2 * 12/2008 Barth et al. .................... 514/326
7,687,537 B2 * 3/2010 Ducoux et al. ................ 514/438

FOREIGN PATENT DOCUMENTS

WO   WO2004/099157 A1   11/2004
WO   WO2005/035488 A2    4/2005
WO   WO2007/046550 A1    4/2007

OTHER PUBLICATIONS

International Preliminary Report on Patentability dated Sep. 27, 2011 issued in PCT/FR2010/050551.
International Search Report dated Aug. 18, 2010 issued in PCT/FR2010/050551.

* cited by examiner

*Primary Examiner* — Golam M M Shameem
(74) *Attorney, Agent, or Firm* — Scully, Scott, Murphy & Presser, P.C.

(57) ABSTRACT

The invention relates to compounds of the formula (I), where: $R_1$ is: a —$NR_5R_6$ group; an unsubstituted or substituted phenyl; $R_2$ is: a ($C_1$-$C_4$)alkyl; an —X—$R_7$ group; $R_3$ and $R_4$ each are independently a substituted phenyl; $R_5$ is a hydrogen atom or a ($C_1$-$C_4$)alkyl; $R_6$ is an unsubstituted or substituted ($C_1$-$C_4$)alkyl; or $R_5$ and $R_6$ together with the nitrogen atom to which they are bonded constitute an unsubstituted or substituted heterocyclic compound; X is a ($C_1$-$C_5$)alkylene; $R_7$ is an —$OR_8$ group, a —$NR_9R_{10}$ group, an —$SO_2$—($C_1$-$C_4$)alkyl group; $R_8$ is a hydrogen atom or a ($C_1$-$C_4$)alkyl; $R_9$ is a hydrogen atom or a ($C_1$-$C_4$)alkyl; $R_{10}$ is a hydrogen atom, a —$COR_{11}$ group, an —$SO_2R_{11}$ group or a —$CO(CH_2)_m$OH group; $R_{11}$ is an unsubstituted or substituted ($C_1$-$C_4$)alkyl; m is 1, 2 or 3. The invention also relates to methods for preparing same and to the therapeutic use thereof.

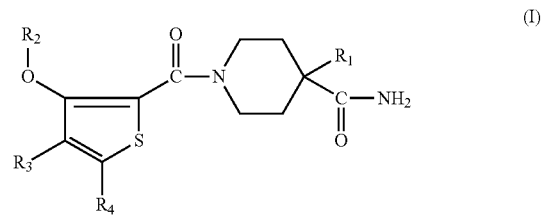

(I)

8 Claims, No Drawings

DERIVATIVES OF 3-ALKOXY-4,5-DIARYLTHIOPHENE-2-CARBOXAMIDE, PREPARATION THEREOF, AND THERAPEUTIC USE THEREOF

The subject of the present invention is 3-alkoxy-4,5-diarylthiophene-2-carboxamide derivatives, the preparation thereof and the therapeutic use thereof.

Diphenylpyrazole derivatives, having an affinity for cannabinoid $CB_1$ receptors, have been described in particular in patents U.S. Pat. No. 5,624,941, EP 0 576 357, EP 0 656 354 and EP 1 150 961.

5,6-Diphenyl-2-pyrazinecarboxamide derivatives are described in International application WO 03/051 850 as $CB_1$ receptor antagonists.

1,2-Diphenyl-4-imidazole carboxamide derivatives are described in International patent application WO 03/027 076 as agonists of $CB_1$ receptors, partial agonists or antagonists.

4,5-Diarylthiophene derivatives having analgesic properties are described in International application WO 91/19 708.

Other 4,5-diarylthiophene derivatives are described in International applications WO 2005/035 488, WO 2006/070 106, WO 2006/077 320 and WO 2006/084 975 as $CB_1$ receptor antagonists.

Novel 3-alkoxy-4,5-diarylthiophene-2-carboxamide derivatives bearing a particular substituent in position 3 of the thiophene ring, which have cannabinoid $CB_1$ receptor antagonist properties, have now been found. In particular, these novel derivatives have antagonist properties with respect to peripheral $CB_1$ receptors and exhibit weak penetration into the brain.

Thus, the subject of the present invention is compounds corresponding to formula (I):

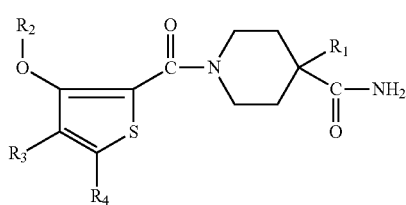

in which:
$R_1$ represents:
  an —$NR_5R_6$ group;
  a phenyl which is unsubstituted or substituted one or more times with substituents chosen independently from a halogen atom, a $(C_1-C_4)$alkyl, a $(C_1-C_4)$alkoxy and a trifluoromethyl;
$R_2$ represents:
  a $(C_1-C_4)$alkyl;
  an —X—$R_7$ group;
$R_3$ and $R_4$ each independently represent a phenyl substituted one or more times with a substituent chosen independently from a halogen atom, a $(C_1-C_4)$alkyl, a $(C_1-C_4)$alkoxy and a trifluoromethyl;
$R_5$ represents a hydrogen atom or a $(C_1-C_4)$alkyl;
$R_6$ represents a $(C_1-C_4)$alkyl which is unsubstituted or substituted with one or more fluorine atoms or with a phenyl which is unsubstituted or substituted with a halogen atom;
or else $R_5$ and $R_6$, together with the nitrogen atom to which they are bonded, constitute a heterocycle chosen from: azetidine, pyrrolidine, and piperidine, said heterocycle being unsubstituted or substituted one or more times with a halogen atom;
X represents a $(C_1-C_5)$alkylene;
$R_7$ represents an —$OR_8$ group, an —$NR_9R_{10}$ group or an —$SO_2$—$(C_1-C_4)$alkyl group;
$R_8$ represents a hydrogen atom or a $(C_1-C_4)$alkyl;
$R_9$ represents a hydrogen atom or a $(C_1-C_4)$alkyl;
$R_{10}$ represents a hydrogen atom, a —$COR_{11}$ group, an —$SO_2R_{11}$ group or a —$CO(CH_2)_mOH$ group;
$R_{11}$ represents a $(C_1-C_4)$alkyl which is unsubstituted or substituted with one or more fluorine atoms;
m represents 1, 2 or 3.

The compounds of formula (I) may comprise one or more asymmetric carbon atoms. They can therefore exist in the form of enantiomers or diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

These salts are advantageously prepared with pharmaceutically acceptable acids, but the salts of other acids that are of use for purifying or isolating the compounds of formula (I) are also part of the invention.

The term "halogen atom" is intended to mean a bromine, chlorine, fluorine or iodine atom.

The term "$(C_1-C_4)$alkyl" is intended to mean a linear or branched alkyl radical containing from one to four carbon atoms, such as the methyl, ethyl, propyl, isopropyl, butyl, isobutyl, sec-butyl or tert-butyl radical.

The term "$(C_1-C_5)$alkylene" is intended to mean a divalent radical containing from two to five carbon atoms, such as the methylene, ethylene, trimethylene or tetramethylene radical or the pentamethylene radical.

The term "$(C_1-C_4)$alkoxy" is intended to mean a linear or branched alkoxy radical containing from one to four carbon atoms, such as the methoxy, ethoxy, propoxy, isopropoxy, butoxy, sec-butoxy or tert-butoxy radical.

The term "$(C_3-C_7)$cycloalkyl" is intended to mean a cyclopropyl, cyclobutyl, cyclopentyl, cyclohexyl or cycloheptyl carbon-based radical.

According to the present invention, preference is given to the compounds of formula (I) in which:
$R_1$ represents:
  an —$NR_5R_6$ group;
  a phenyl;
$R_2$ represents:
  a methyl;
  an —X—$R_7$ group;
$R_3$ and $R_4$ each independently represent a phenyl substituted once or twice with a halogen atom;
$R_5$ represents a hydrogen atom;
$R_6$ represents a $(C_1-C_4)$alkyl substituted with one or more fluorine atoms or with a phenyl which is unsubstituted or substituted with a halogen atom;
or else $R_5$ and $R_6$, together with the nitrogen atom to which they are bonded, constitute a piperidin-1-yl radical which is unsubstituted or substituted once or twice with a halogen atom;
X represents a $(C_1-C_3)$alkylene;
$R_7$ represents an —$OR_8$ group, an —$NR_9R_{10}$ group or an —$SO_2$—$CH_3$ group;

$R_8$ represents a hydrogen atom;
$R_9$ represents a hydrogen atom;
$R_{10}$ represents a hydrogen atom, a —CO—CH$_3$ group, an —SO$_2$—CH$_3$ group or a —COCH$_2$OH group; in the form of a base or of an addition salt with an acid.

In particular, preference is given to the compounds of formula (I) in which:

$R_1$ represents:
an —NH(CH$_2$)$_2$—CF$_3$ group, a 4-fluorobenzylamino group, a benzylamino group, a piperidin-1-yl radical, a 4,4-difluoropiperidin-1-yl radical;
a phenyl;

$R_2$ represents:
a methyl;
an —X—R$_7$ group;
$R_3$ represents a 4-chlorophenyl;
$R_4$ represents a 2-chlorophenyl or a 2,4-dichlorophenyl;
X represents a methylene, an ethylene or a trimethylene;
$R_7$ represents an —OH radical, an —NH$_2$ radical, an —NHCOCH$_3$ group, an —NHSO$_2$CH$_3$ group, an —NHCOCH$_2$OH group or an —SO$_2$—CH$_3$ group; in the form of a base or of an addition salt with an acid.

Among the compounds according to the invention, mention may in particular be made of the compounds hereinafter, as they are and also their salts:

| IUPAC name | Chemical structure |
| --- | --- |
| 1<br>1'-{[4-(4-chlorophenyl)-5-(2,4-dichlorophenyl)-3-methoxythien-2-yl]carbonyl}-1,4'-bipiperidine-4'-carboxamide | 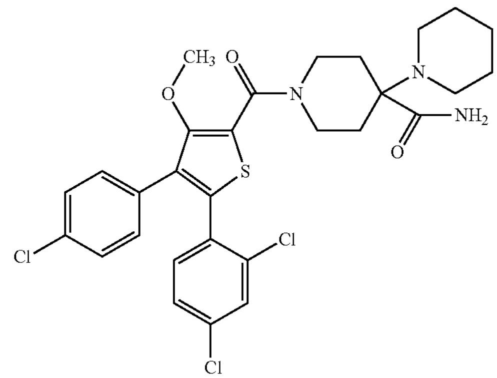 [SMILES: COc1c(C(=O)N2CCC(C(N)=O)(N3CCCCC3)CC2)sc(-c2ccc(Cl)cc2Cl)c1-c1ccc(Cl)cc1] |
| 2<br>1'-{[4-(4-chlorophenyl)-5-(2,4-dichlorophenyl)-3-{3-[(methylsulfonyl)amino]propoxy}thien-2-yl]carbonyl}-1,4'-bipiperidine-4'-carboxamide | 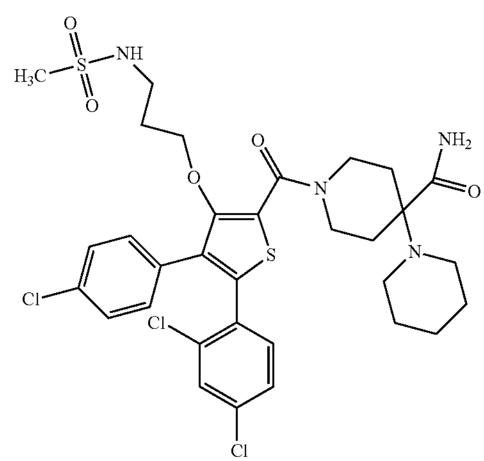 [SMILES: CS(=O)(=O)NCCCOc1c(C(=O)N2CCC(C(N)=O)(N3CCCCC3)CC2)sc(-c2ccc(Cl)cc2Cl)c1-c1ccc(Cl)cc1] |

| IUPAC name | Chemical structure |
|---|---|
| 3<br>1'-({4-(4-chlorophenyl)-5-(2,4-dichlorophenyl)-3-[3-(methylsulfonyl)propoxy]thien-2-yl}carbonyl)-1,4'-bipiperidine-4'-carboxamide | 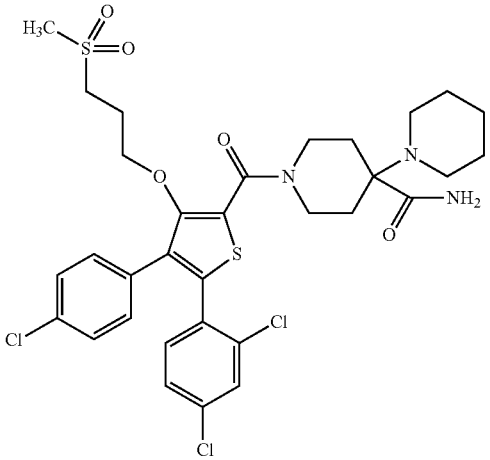 [SMILES: CS(=O)(=O)CCCOc1c(C(=O)N2CCC(C(N)=O)(N3CCCCC3)CC2)sc(-c2ccc(Cl)cc2Cl)c1-c1ccc(Cl)cc1] |
| 4<br>1-{[4-(4-chlorophenyl)-5-(2,4-dichlorophenyl)-3-(3-hydroxypropoxy)thien-2-yl]carbonyl}-4-phenylpiperidine-4-carboxamide | 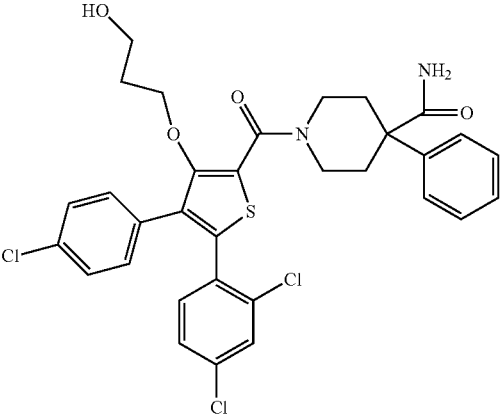 [SMILES: NC(=O)C1(c2ccccc2)CCN(C(=O)c2sc(-c3ccc(Cl)cc3Cl)c(-c3ccc(Cl)cc3)c2OCCCO)CC1] |
| 5<br>1-({4-(4-chlorophenyl)-5-(2,4-dichlorophenyl)-3-[3-(methylsulfonyl)propoxy]thien-2-yl}carbonyl)-4-phenylpiperidine-4-carboxamide | 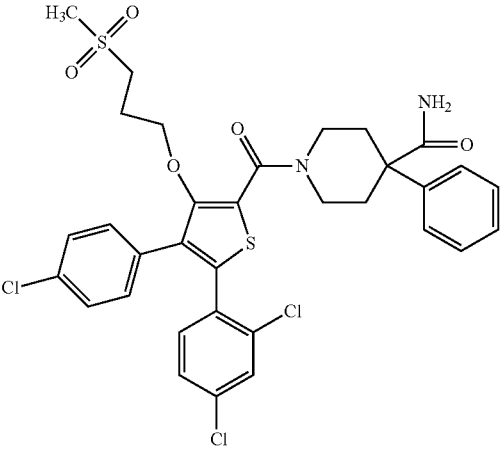 [SMILES: CS(=O)(=O)CCCOc1c(C(=O)N2CCC(C(N)=O)(c3ccccc3)CC2)sc(-c2ccc(Cl)cc2Cl)c1-c1ccc(Cl)cc1] |

-continued

| IUPAC name | Chemical structure |
|---|---|
| 6<br>1-{[4-(4-chlorophenyl)-5-(2,4-dichlorophenyl)-3-(2-hydroxyethoxy)thien-2-yl]carbonyl}-4-phenylpiperidine-4-carboxamide | 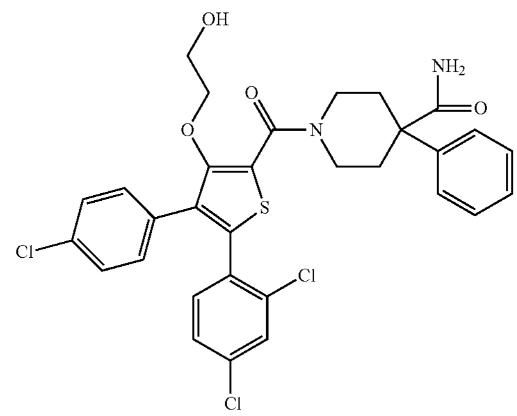 [SMILES: NC(=O)C1(c2ccccc2)CCN(C(=O)c2sc(-c3ccc(Cl)cc3Cl)c(-c3ccc(Cl)cc3)c2OCCO)CC1] |
| 7<br>1'-{[4-(4-chlorophenyl)-5-(2,4-dichlorophenyl)-3-(2-hydroxyethoxy)thien-2-yl]carbonyl}-4,4-difluoro-1,4'-bipiperidine-4'-carboxamide | 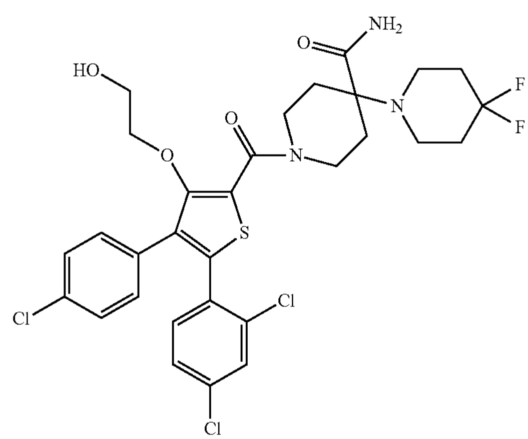 [SMILES: NC(=O)C1(N2CCC(F)(F)CC2)CCN(C(=O)c2sc(-c3ccc(Cl)cc3Cl)c(-c3ccc(Cl)cc3)c2OCCO)CC1] |
| 8<br>1'-({4-(4-chlorophenyl)-5-(2,4-dichlorophenyl)-3-[3-(methylsulfonyl)propoxy]thien-2-yl}carbonyl)-4,4-difluoro-1,4'-bipiperidine-4'-carboxamide | 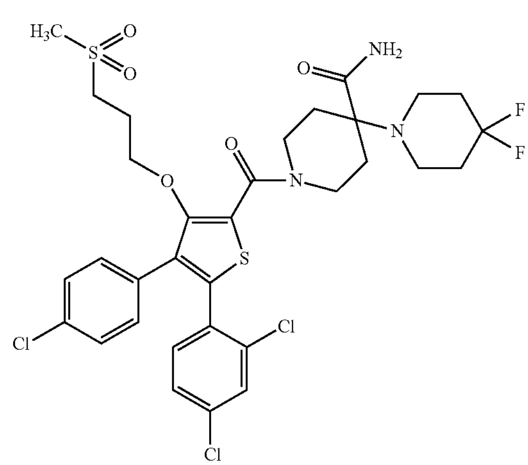 [SMILES: CS(=O)(=O)CCCOc1c(C(=O)N2CCC(C(N)=O)(N3CCC(F)(F)CC3)CC2)sc(-c2ccc(Cl)cc2Cl)c1-c1ccc(Cl)cc1] |

| IUPAC name | Chemical structure |
|---|---|
| 9<br>1'-{[4-(4-chlorophenyl)-5-(2,4-dichlorophenyl)-3-(3-hydroxypropoxy)thien-2-yl]carbonyl}-4,4-difluoro-1,4'-bipiperidine-4'-carboxamide | 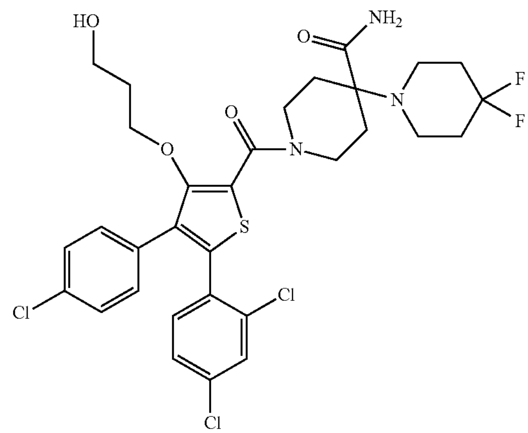 [SMILES: NC(=O)C1(N2CCC(F)(F)CC2)CCN(C(=O)c2sc(-c3ccc(Cl)cc3Cl)c(-c3ccc(Cl)cc3)c2OCCCO)CC1] |
| 10<br>1-{[4-(4-chlorophenyl)-5-(2,4-dichlorophenyl)-3-(2-hydroxyethoxy)thien-2-yl]carbonyl}-4-[(3,3,3-trifluoropropyl)amino]piperidine-4-carboxamide | 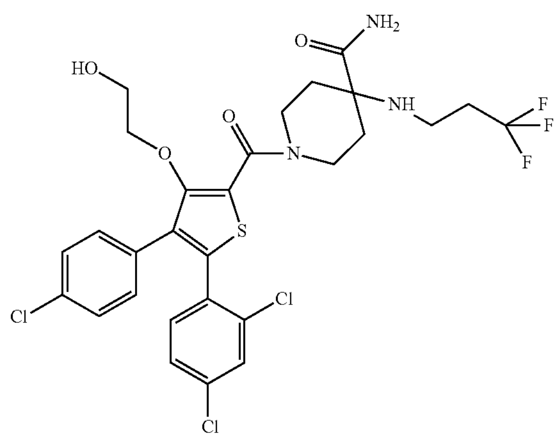 [SMILES: NC(=O)C1(NCCC(F)(F)F)CCN(C(=O)c2sc(-c3ccc(Cl)cc3Cl)c(-c3ccc(Cl)cc3)c2OCCO)CC1] |
| 11<br>1-({4-(4-chlorophenyl)-5-(2,4-dichlorophenyl)-3-[3-(methylsulfonyl)propoxy]thien-2-yl}carbonyl)-4-[(3,3,3-trifluoropropyl)amino]piperidine-4-carboxamide | 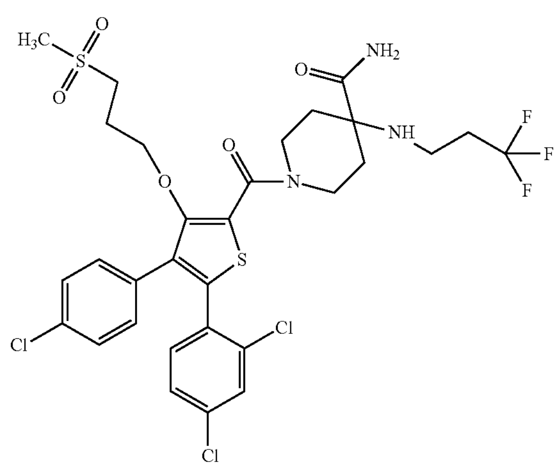 [SMILES: CS(=O)(=O)CCCOc1c(C(=O)N2CCC(NCCC(F)(F)F)(C(N)=O)CC2)sc(-c2ccc(Cl)cc2Cl)c1-c1ccc(Cl)cc1] |

-continued

| IUPAC name | Chemical structure |
|---|---|
| 12<br>1-{[4-(4-chlorophenyl)-5-(2,4-dichlorophenyl)-3-{2-[(hydroxyacetyl)amino]ethoxy}thien-2-yl]carbonyl}-4-[(3,3,3-trifluoropropyl)amino]piperidine-4-carboxamide | 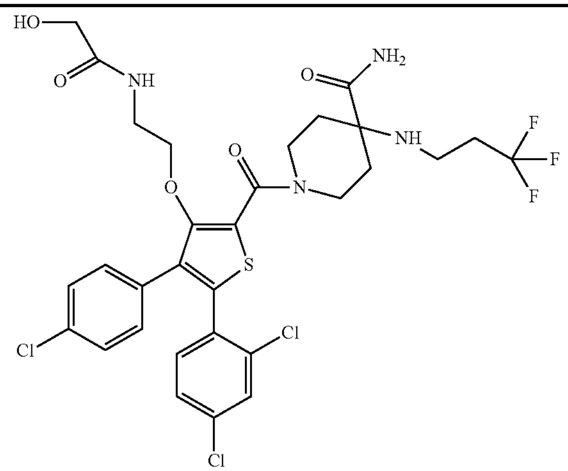 |
| 13<br>1-{[4-(4-chlorophenyl)-5-(2,4-dichlorophenyl)-3-(3-hydroxypropoxy)thien-2-yl]carbonyl}-4-[(3,3,3-trifluoropropyl)amino]piperidine-4-carboxamide | 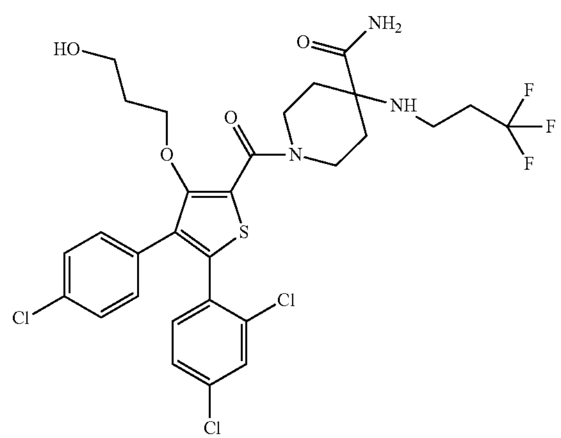 [SMILES: NC(=O)C1(NCCC(F)(F)F)CCN(C(=O)c2sc(-c3ccc(Cl)cc3Cl)c(-c3ccc(Cl)cc3)c2OCCCO)CC1] |
| 14<br>1-{[4-(4-chlorophenyl)-5-(2,4-dichlorophenyl)-3-{2-[(hydroxyacetyl)amino]ethoxy}thien-2-yl]carbonyl}-4-phenylpiperidine-4-carboxamide | 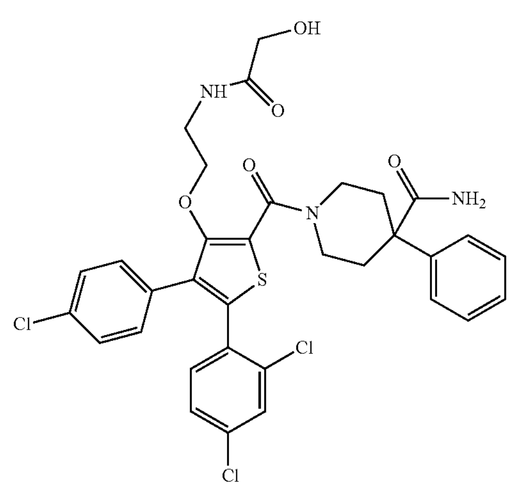 [SMILES: NC(=O)C1(c2ccccc2)CCN(C(=O)c2sc(-c3ccc(Cl)cc3Cl)c(-c3ccc(Cl)cc3)c2OCCNC(=O)CO)CC1] |

| IUPAC name | Chemical structure |
| --- | --- |
| 15<br>1-{[3-(2-acetamidoethoxy)-4-(4-chlorophenyl)-5-(2,4-dichlorophenyl)thien-2-yl]carbonyl}-4-phenylpiperidine-4-carboxamide | 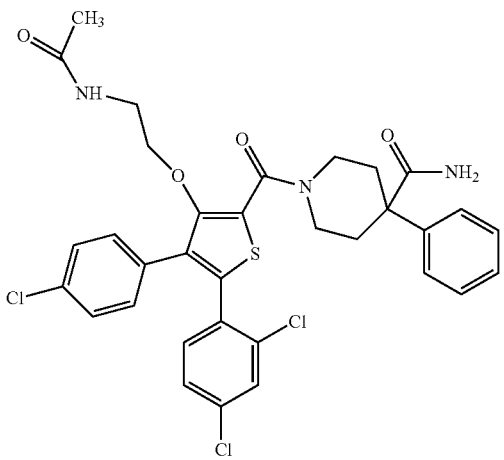 [SMILES: CC(=O)NCCOc1c(C(=O)N2CCC(C(N)=O)(c3ccccc3)CC2)sc(-c2ccc(Cl)cc2Cl)c1-c1ccc(Cl)cc1] |
| 16<br>1-{[4-(4-chlorophenyl)-5-(2,4-dichlorophenyl)-3-(2-hydroxyethoxy)thien-2-yl]carbonyl}-4-[(4-fluorobenzyl)amino]piperidine-4-carboxamide | 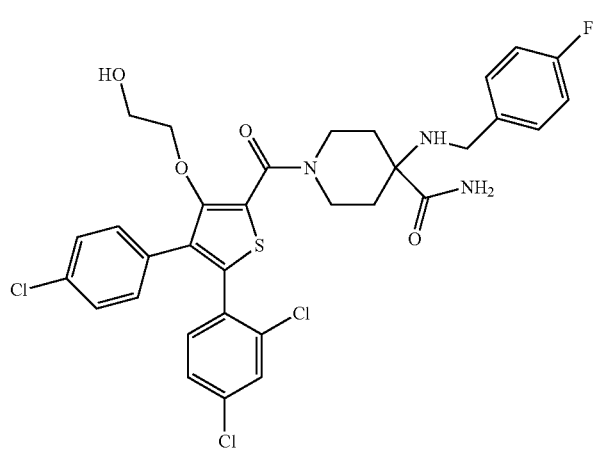 [SMILES: NC(=O)C1(NCc2ccc(F)cc2)CCN(C(=O)c2sc(-c3ccc(Cl)cc3Cl)c(-c3ccc(Cl)cc3)c2OCCO)CC1] |
| 17<br>1-{[4-(4-chlorophenyl)-5-(2,4-dichlorophenyl)-3-(3-hydroxypropoxy)thien-2-yl]carbonyl}-4-[(4-fluorobenzyl)amino]piperidine-4-carboxamide | 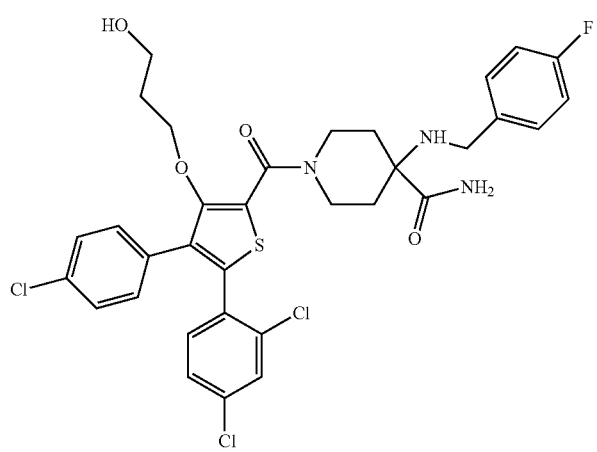 [SMILES: NC(=O)C1(NCc2ccc(F)cc2)CCN(C(=O)c2sc(-c3ccc(Cl)cc3Cl)c(-c3ccc(Cl)cc3)c2OCCCO)CC1] |

-continued

| IUPAC name | Chemical structure |
|---|---|
| 18<br>1-({4-(4-chlorophenyl)-5-(2,4-dichlorophenyl)-3-[3-(methylsulfonyl)propoxy]thien-2-yl}carbonyl)-4-[(4-fluorobenzyl)amino]piperidine-4-carboxamide | 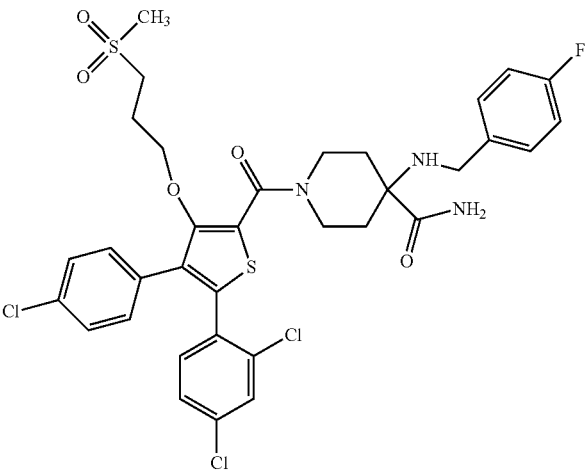 [SMILES: CS(=O)(=O)CCCOc1c(C(=O)N2CCC(NCc3ccc(F)cc3)(C(N)=O)CC2)sc(-c2ccc(Cl)cc2Cl)c1-c1ccc(Cl)cc1] |
| 19<br>1-{[3-(2-acetamidoethoxy)-4-(4-chlorophenyl)-5-(2,4-dichlorophenyl)thien-2-yl]carbonyl}-4-[(4-fluorobenzyl)amino]piperidine-4-carboxamide | 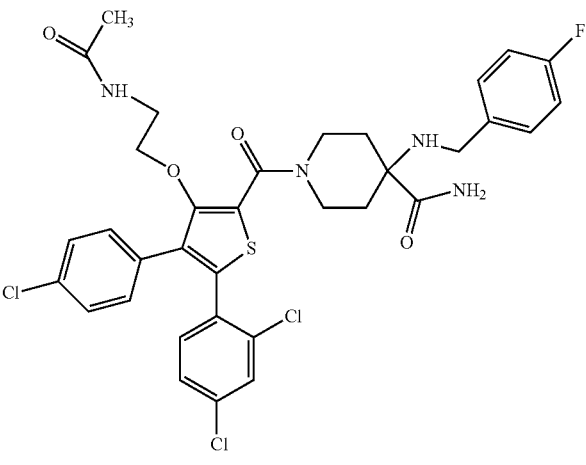 [SMILES: CC(=O)NCCOc1c(C(=O)N2CCC(NCc3ccc(F)cc3)(C(N)=O)CC2)sc(-c2ccc(Cl)cc2Cl)c1-c1ccc(Cl)cc1] |
| 20<br>1-{[4-(4-chlorophenyl)-5-(2,4-dichlorophenyl)-3-{2-[(hydroxyacetyl)amino]ethoxy}thien-2-yl]carbonyl}-4-[(4-fluorobenzyl)amino]piperidine-4-carboxamide | 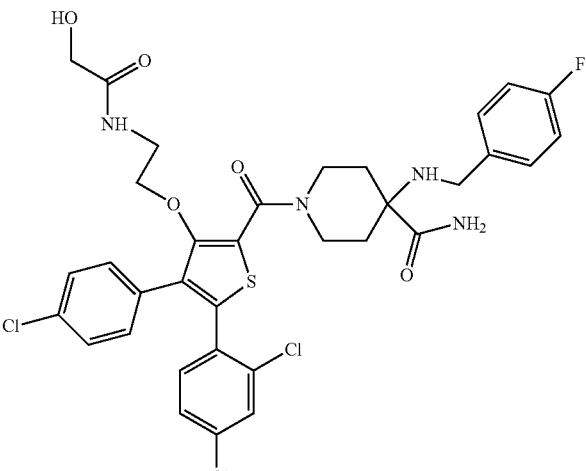 |

-continued

| IUPAC name | Chemical structure |
|---|---|
| 21<br>1-{[4-(4-chlorophenyl)-5-(2,4-dichlorophenyl)-3-{3-[(hydroxyacetyl)amino]propoxy}thien-2-yl]carbonyl}-4-[(4-fluorobenzyl)amino]piperidine-4-carboxamide | 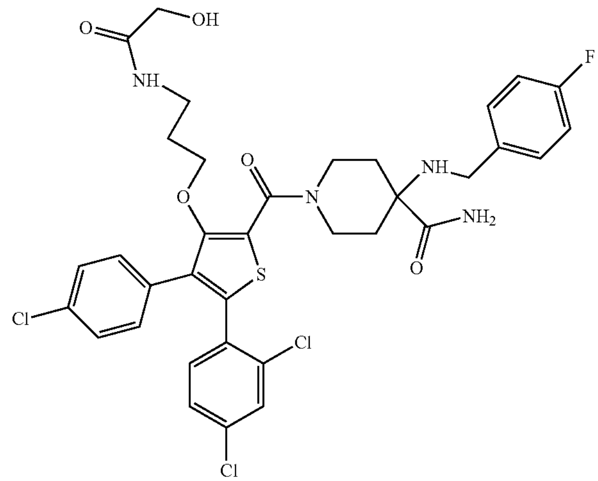 [SMILES: NC(=O)C1(NCc2ccc(F)cc2)CCN(C(=O)c2sc(-c3ccc(Cl)cc3Cl)c(-c3ccc(Cl)cc3)c2OCCCNC(=O)CO)CC1] |
| 22<br>1-{[3-(3-acetamidopropoxy)-4-(4-chlorophenyl)-5-(2,4-dichlorophenyl)thien-2-yl]carbonyl}-4-[(4-fluorobenzyl)amino]piperidine-4-carboxamide | 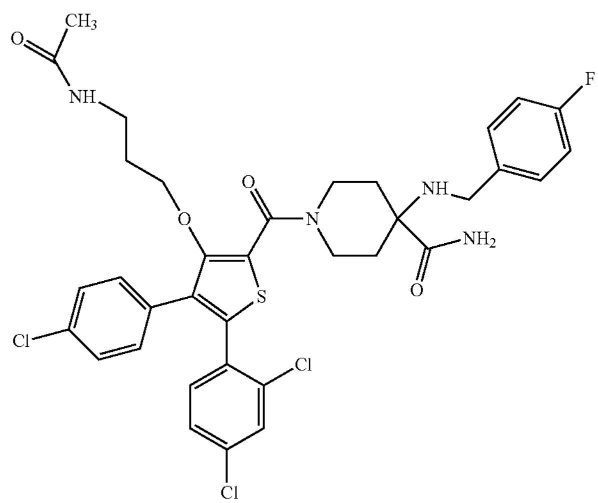 [SMILES: CC(=O)NCCCOc1c(C(=O)N2CCC(NCc3ccc(F)cc3)(C(N)=O)CC2)sc(-c2ccc(Cl)cc2Cl)c1-c1ccc(Cl)cc1] |
| 23<br>4-(benzylamino)-1-{[4-(4-chlorophenyl)-5-(2,4-dichlorophenyl)-3-(2-hydroxyethoxy)thien-2-yl]carbonyl}piperidine-4-carboxamide | 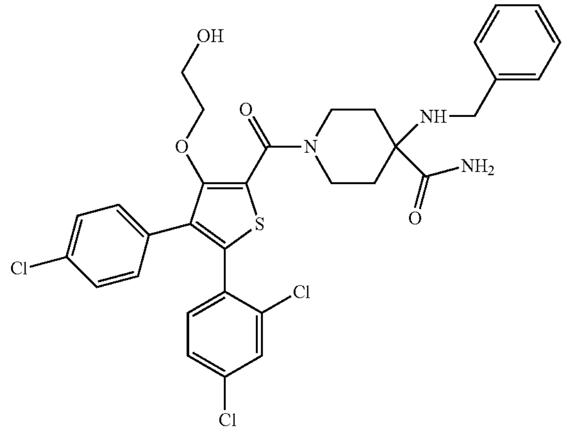 [SMILES: NC(=O)C1(NCc2ccccc2)CCN(C(=O)c2sc(-c3ccc(Cl)cc3Cl)c(-c3ccc(Cl)cc3)c2OCCO)CC1] |

-continued

| IUPAC name | Chemical structure |
|---|---|
| 24<br>4-(benzylamino)-1-{[4-(4-chlorophenyl)-5-(2,4-dichlorophenyl)-3-(3-hydroxypropoxy)thien-2-yl]carbonyl}piperidine-4-carboxamide | 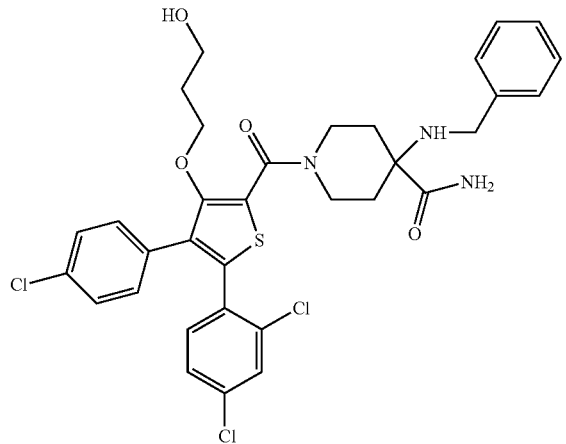 [SMILES: NC(=O)C1(NCc2ccccc2)CCN(C(=O)c2sc(-c3ccc(Cl)cc3Cl)c(-c3ccc(Cl)cc3)c2OCCCO)CC1] |
| 25<br>4-(benzylamino)-1-{[4-(4-chlorophenyl)-5-(2,4-dichlorophenyl)-3-{2-[(hydroxyacetyl)amino]ethoxy}thien-2-yl]carbonyl}piperidine-4-carboxamide | 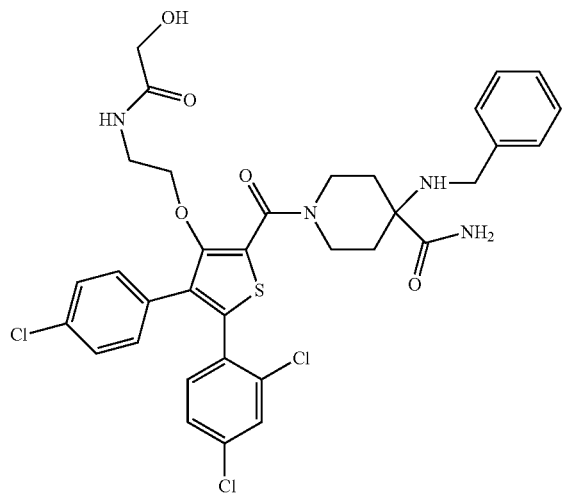 [SMILES: NC(=O)C1(NCc2ccccc2)CCN(C(=O)c2sc(-c3ccc(Cl)cc3Cl)c(-c3ccc(Cl)cc3)c2OCCNC(=O)CO)CC1] |
| 26<br>1-{[5-(2-chlorophenyl)-4-(4-chlorophenyl)-3-(3-hydroxypropoxy)thien-2-yl]carbonyl}-4-[(4-fluorobenzyl)amino]piperidine-4-carboxamide | 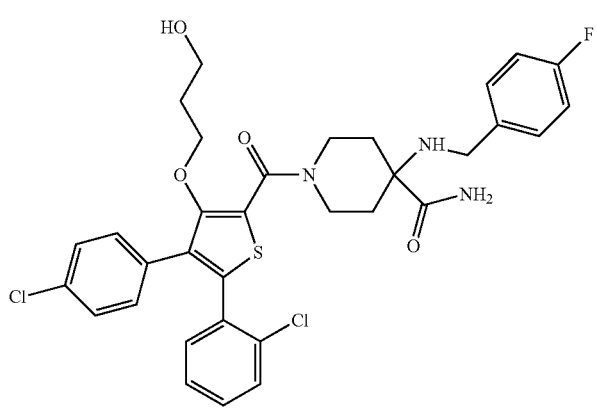 [SMILES: NC(=O)C1(NCc2ccc(F)cc2)CCN(C(=O)c2sc(-c3ccccc3Cl)c(-c3ccc(Cl)cc3)c2OCCCO)CC1] |

| IUPAC name | Chemical structure |
|---|---|
| 27<br>1-{[5-(2-chlorophenyl)-4-(4-chlorophenyl)-3-(3-hydroxypropoxy)thien-2-yl]carbonyl}-4-phenylpiperidine-4-carboxamide | 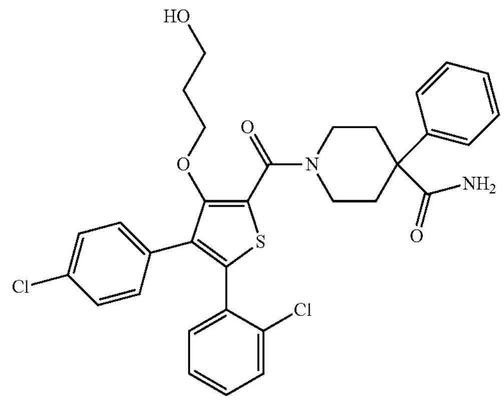 [SMILES: NC(=O)C1(c2ccccc2)CCN(C(=O)c2sc(-c3ccccc3Cl)c(-c3ccc(Cl)cc3)c2OCCCO)CC1] |
| 28<br>1-{[5-(2-chlorophenyl)-4-(4-chlorophenyl)-3-(2-hydroxyethoxy)thien-2-yl]carbonyl}-4-phenylpiperidine-4-carboxamide | 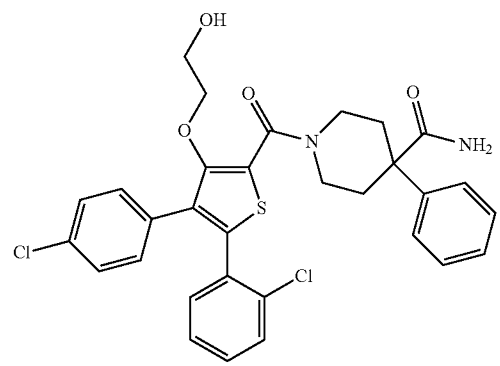 [SMILES: NC(=O)C1(c2ccccc2)CCN(C(=O)c2sc(-c3ccccc3Cl)c(-c3ccc(Cl)cc3)c2OCCO)CC1] |
| 29<br>1-{[5-(2-chlorophenyl)-4-(4-chlorophenyl)-3-(2-hydroxyethoxy)thien-2-yl]carbonyl}-4-[(4-fluorobenzyl)amino]piperidine-4-carboxamide | 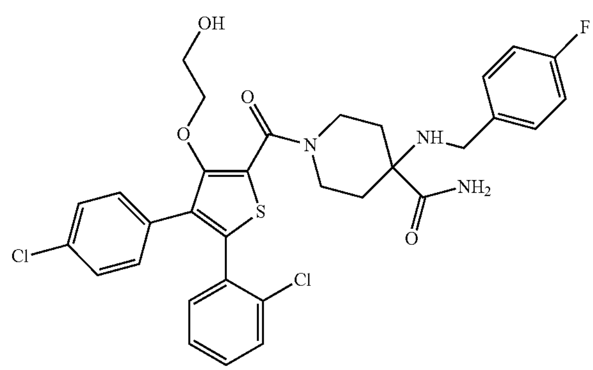 [SMILES: NC(=O)C1(NCc2ccc(F)cc2)CCN(C(=O)c2sc(-c3ccccc3Cl)c(-c3ccc(Cl)cc3)c2OCCO)CC1] |
| 30<br>1-{[3-(2-aminoethoxy)-5-(2-chlorophenyl)-4-(4-chlorophenyl)thien-2-yl]carbonyl}-4-[(4-fluorobenzyl)amino]piperidine-4-carboxamide | 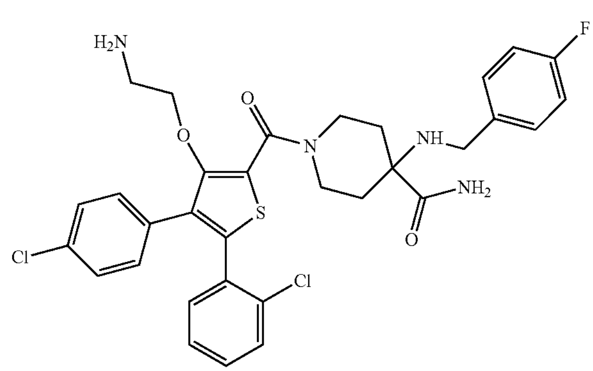 [SMILES: NCCOc1c(C(=O)N2CCC(NCc3ccc(F)cc3)(C(N)=O)CC2)sc(-c2ccccc2Cl)c1-c1ccc(Cl)cc1] |

| IUPAC name | Chemical structure |
|---|---|
| 31<br>1-{[3-(2-acetamidoethoxy)-5-(2-chlorophenyl)-4-(4-chlorophenyl)thien-2-yl]carbonyl}-4-[(4-fluorobenzyl)amino]piperidine-4-carboxamide | 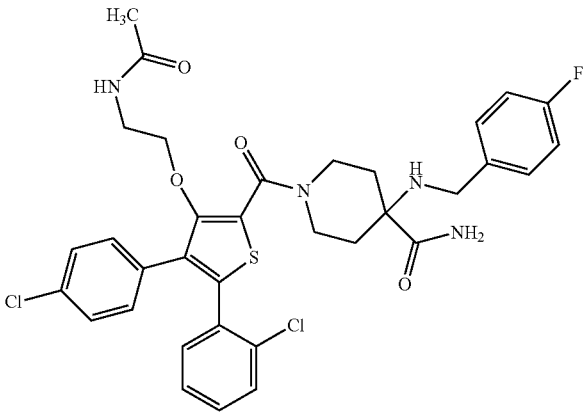 [SMILES: CC(=O)NCCOc1c(C(=O)N2CCC(NCc3ccc(F)cc3)(C(N)=O)CC2)sc(-c2ccccc2Cl)c1-c1ccc(Cl)cc1] |
| 32<br>1-{[3-(2-aminoethoxy)-5-(2-chlorophenyl)-4-(4-chlorophenyl)thien-2-yl]carbonyl}-4-phenylpiperidine-4-carboxamide | 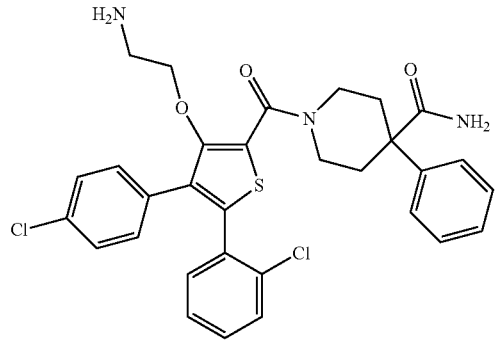 [SMILES: NCCOc1c(C(=O)N2CCC(C(N)=O)(c3ccccc3)CC2)sc(-c2ccccc2Cl)c1-c1ccc(Cl)cc1] |
| 33<br>1-{[5-(2-chlorophenyl)-4-(4-chlorophenyl)-3-{2-[(hydroxyacetyl)amino]ethoxy}thien-2-yl]carbonyl}-4-phenylpiperidine-4-carboxamide | 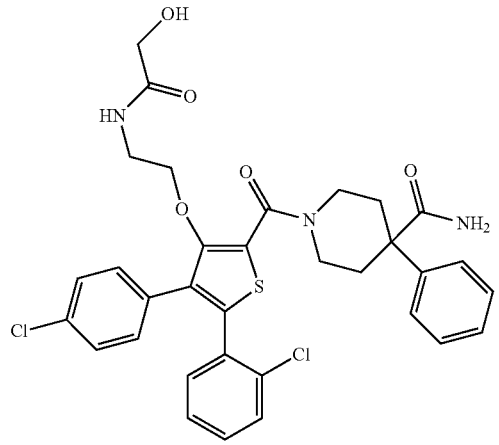 [SMILES: NC(=O)C1(c2ccccc2)CCN(C(=O)c2sc(-c3ccccc3Cl)c(-c3ccc(Cl)cc3)c2OCCNC(=O)CO)CC1] |
| 34<br>1-{[3-(2-acetamidoethoxy)-5-(2-chlorophenyl)-4-(4-chlorophenyl)thien-2-yl]carbonyl}-4-phenylpiperidine-4-carboxamide | 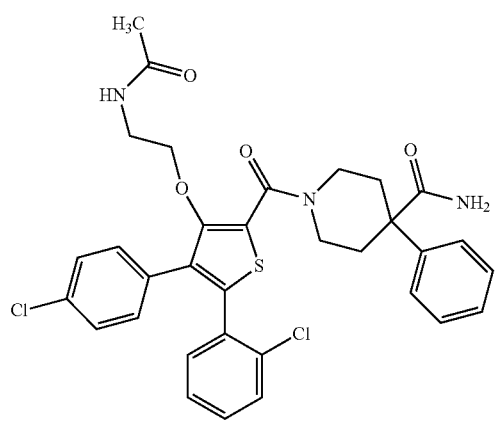 [SMILES: CC(=O)NCCOc1c(C(=O)N2CCC(C(N)=O)(c3ccccc3)CC2)sc(-c2ccccc2Cl)c1-c1ccc(Cl)cc1] |

| IUPAC name | Chemical structure |
|---|---|
| 35<br>1-{[5-(2-chlorophenyl)-4-(4-chlorophenyl)-3-{2-[(hydroxyacetyl)amino]ethoxy}thien-2-yl]carbonyl}-4-[(4-fluorobenzyl)amino]piperidine-4-carboxamide | |

In the following text, the term "protective group Pg" is intended to mean a group which makes it possible, firstly, to protect a reactive function such as a hydroxyl or an amine during a synthesis and, secondly, to regenerate the intact reactive function at the end of the synthesis. Examples of protective groups and also methods of protection and of deprotection are given in "Protective Group in Organic Synthesis", Green et al., 4th edition, John Wiley & Sons, Inc., New York, 2007.

In the following text, the term "leaving group" is intended to mean a group that can be readily cleaved from a molecule by breaking a heterolytic bond, with the departure of a pair of electrons. This group can thus be readily replaced with another group during a substitution reaction, for example. Such leaving groups are, for example, halogens or an activated hydroxyl group, such as a methanesulfonate, benzenesulfonate, p-toluenesulfonate, triflate, acetate, etc. Examples of leaving groups and also references for the preparation thereof are given in "Advanced Organic Chemistry", M. B. Smith and J. March, 6th edition, Wiley Interscience, 2007, p. 496-501.

In accordance with the invention, the compounds of formula (I) can be prepared according to a process which is characterized in that:

A compound of formula:

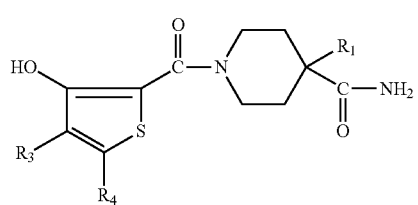

(II)

in which $R_1$, $R_3$ and $R_4$ are as defined for a compound of formula (I), is reacted, in the presence of a base, with a compound of formula:

Z—$R_2$ (III)

in which $R_2$ is as defined for a compound of formula (I) and Z represents a leaving group as previously described.

Optionally, the compound of formula (I) is converted into one of its addition salts with an acid.

The reaction is carried out in the presence of a base, such as an alkali metal carbonate, cesium carbonate or sodium carbonate for example, in a solvent such as acetone, acetonitrile or N,N-dimethylformamide and at a temperature between ambient temperature and the reflux temperature of the solvent.

According to one variant of the process:

An acid or a functional derivative of this acid of formula:

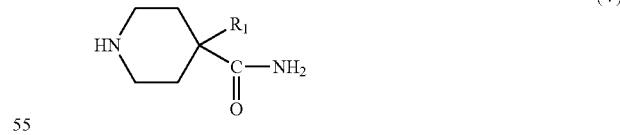

(IV)

in which $R_2$, $R_3$ and $R_4$ are as defined for a compound of formula (I), is reacted with a compound of formula:

(V)

in which $R_1$ is as defined for a compound of formula (I).

Optionally, the compound of formula (I) thus obtained is converted into one of its salts.

When a compound of formula (V) is treated with the acid of formula (IV) itself, the process is carried out in the presence of a coupling agent used in peptide chemistry, such as 1,3-dicyclohexylcarbodiimide or benzotriazol-1-yloxytris(dimethylamino)phosphonium hexafluorophosphate or benzotriazol-1-yloxytris(pyrrolidino)phosphonium hexafluorophosphate or 2-(1H-benzotriazol-1-yl)-1,1,3,3-tetramethyluronium tetrafluoroborate, in the presence of a base such as triethylamine, N,N-diisopropylethylamine or 4-dimethylaminopyridine, in a solvent such as dichloromethane, dichloroethane, N,N-dimethylformamide or tetrahydrofuran, at a temperature between −10° C. and the reflux temperature of the solvent.

As functional derivative of the acid (IV), use may be made of the acid chloride, the anhydride, in mixed anhydride, a $C_1$-$C_4$ alkyl ester in which the alkyl is straight or branched, or an activated ester, for example the p-nitrophenyl ester.

In the process according to the invention, therefore, the acid chloride obtained by reacting thionyl chloride or oxalyl chloride with the acid of formula (IV) can also be reacted with the compound of formula (V), in a solvent, such as a chlorinated solvent (dichloromethane, dichloroethane or chloroform for example), an ether (tetrahydrofuran or dioxane for example), or an amide (N,N-dimethylformamide for example) under an inert atmosphere, at a temperature between 0° C. and ambient temperature, in the presence of a tertiary amine such as triethylamine, N-methylmorpholine or pyridine.

One variant consists in preparing the mixed anhydride of the acid of formula (IV) by reacting ethyl chloroformate with the acid of formula (IV), in the presence of a base such as triethylamine, and in reacting it with the compound of formula (V), in a solvent such as dichloromethane, under an inert atmosphere, at ambient temperature, in the presence of a base such as triethylamine.

According to another variant of the process, the compounds of formula (I) in which $R_2$ represents an —X—$R_7$ group and $R_7$ represents an —$NR_9R_{10}$ group with $R_{10}$=—$COR_{11}$ or with $R_{10}$=—$CO(CH_2)_mOH$ can be prepared from a compound of formula (I) in which X—$NR_9R_{10}$=X—$NR_9H$. The latter compound is reacted with an acid of formula $R_{11}$—COOH (VI) or, respectively, with an acid of formula HO—$(CH_2)_mCOOH$ (VII) according to the operating conditions previously described for reacting an acid of formula (IV) with the compound of formula (V).

According to another variant of the process, the compounds of formula (I) in which $R_2$ represents an —X—$R_7$ group and $R_7$ represents an —$NR_9R_{10}$ group with $R_{10}$=—$SO_2R_{11}$ can be prepared from a compound of formula (I) in which X—$NR_9R_{10}$=X—$NR_9H$. The latter compound is reacted with a compound of formula Hal-$SO_2R_{11}$ (VIII) in which Hal represents a halogen atom, preferably chlorine. The reaction is carried out in the presence of a base such as triethylamine, in a solvent such as dichloromethane, and at a temperature between 0° C. and ambient temperature.

The compounds of formula (I) obtained via the various procedures can be subsequently separated from the reaction medium and purified according to conventional methods, for example by crystallization or chromatography.

The compounds of formula (II) are prepared by reacting a compound of formula:

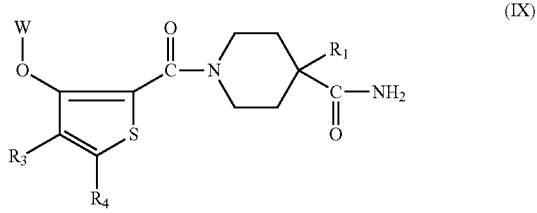

(IX)

in which $R_1$, $R_3$ and $R_4$ are as defined for a compound of formula (I) and W represents a ($C_1$-$C_4$)alkyl, with, for example, tribromoborane, in a solvent such as, for example, dichloromethane and at a temperature between −60° C. and ambient temperature.

The compounds of formula (III) are known, are commercially available or are prepared according to methods known to those skilled in the art.

The compounds of formula (IV) are prepared by saponification of a compound of formula:

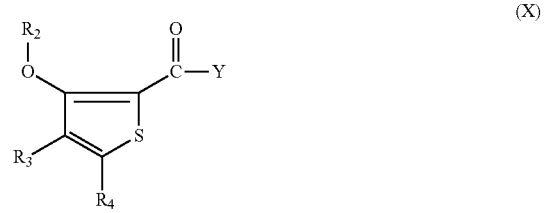

(X)

in which $R_2$, $R_3$ and $R_4$ are as defined for a compound of formula (I) and Y represents a ($C_1$-$C_2$)alkoxy group. Thus, for example, when Y=—$OCH_3$, the reaction is carried out by the action of sodium hydroxide, in a solvent such as methanol, N,N-dimethylformamide or a mixture of these solvents, and at a temperature between ambient temperature and the reflux temperature of the solvent.

The compounds of formula (V) are known or are prepared according to known methods, such as those described in EP 0 428 434, EP 0 512 901, EP 0 515 240, WO 96/23 787, WO 02/094 821, WO 03/104 225 and WO 2006/021 654 or in J. Med. Chem., 1964, 7, 619-622 and J. Org. Chem., 1990, 55, 4207-4209.

The compounds of formula (V) are generally prepared in a form protected on the nitrogen atom of the piperidine; after a deprotection step, the expected compounds of formula (V) are obtained.

The compounds of formulae (VI), (VII) and (VIII) are known, are commercially available or are prepared according to methods known to those skilled in the art.

The compounds of formula (IX) are prepared by reacting an acid or a functional derivative of this acid of formula:

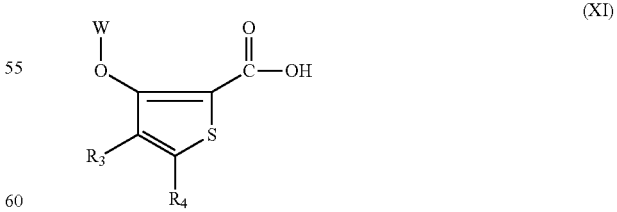

(XI)

in which $R_3$ and $R_4$ are as defined for a compound of formula (I) and W represents a ($C_1$-$C_4$)alkyl, with a compound of formula (V) according to the operating conditions previously described for reacting a compound of formula (IV) with the compound of formula (V).

The compounds of formula (X) are prepared by reacting a compound of formula:

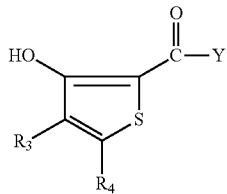

(XII)

in which $R_3$ and $R_4$ are as defined for a compound of formula (I) and Y represents a $(C_1-C_2)$alkoxy, with a compound of formula (III) according to the operating conditions previously described for reacting a compound of formula (II) with the compound of formula (III).

The compounds of formula (XI) are prepared by saponification of a compound of formula:

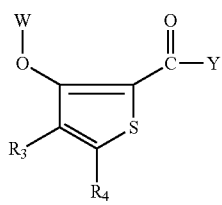

(XIII)

in which $R_3$ and $R_4$ are as defined for a compound of formula (I), W represents a $(C_1-C_4)$alkyl and Y represents a $(C_1-C_2)$alkoxy, according to the methods previously described for the saponification of a compound of formula (X).

The compounds of formula (XII) are prepared by reacting a compound of formula (XIII) with, for example, tribromoborane according to the operating conditions previously described for preparing a compound of formula (II).

The compounds of formula (XIII) are prepared according to SCHEME I hereinafter in which Hal represents a halogen atom, preferably bromine, Y represents a $(C_1-C_2)$alkoxy and W represents a $(C_1-C_4)$alkyl, preferably a methyl.

SCHEME I

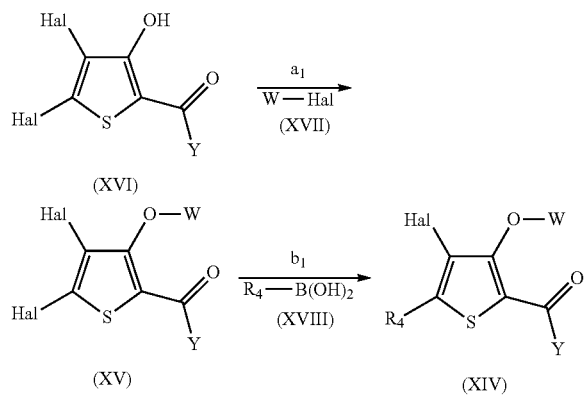

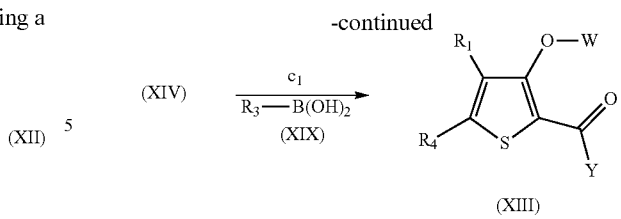

In step a1 of scheme I, a compound of formula (XVI) is reacted with a compound of formula W-Hal (XVII) in the presence of a base, such as an alkali metal carbonate, potassium carbonate for example, in a solvent such as N,N-dimethylformamide and at a temperature between ambient temperature and the reflux temperature of the solvent.

In step b1, the compound of formula (XV) thus obtained is reacted with a boronic acid of formula $R_4$—$B(OH)_2$ (XVIII) in a basic medium for example in the presence of an alkali metal carbonate, such as sodium carbonate for example, and in the presence of a palladium complex such as, for example, tetrakis(triphenylphosphine)-palladium, in a solvent such as toluene, tetrahydrofuran or dioxane and at a temperature between ambient temperature and the reflux temperature of the solvent.

In step c1, the compound of formula (XIV) thus obtained is reacted with a boronic acid of formula $R_3$—$B(OH)_2$ (XIX) according to the conditions previously described in step b1.

The compounds of formulae (XVI), (XVII), (XVIII) and (XIX) are known, are commercially available or are prepared according to methods known to those skilled in the art.

The following examples describe the preparation of certain compounds in accordance with the invention. These examples are not limiting and merely illustrate the present invention. The numbers of the compounds exemplified refer back to those given in TABLES (I) and (II) hereinafter, which illustrate the chemical structures and the physical properties of some compounds according to the invention.

The following abbreviations are used in the Preparations and in the Examples:
EtOAc: ethyl acetate
$BBR_3$: boron tribromide
$Cs_2CO_3$: cesium carbonate
DCM: dichloromethane
DMSO: dimethyl sulfoxide
DMF: N,N-dimethylformamide
Bp: boiling point
Ether: diethyl ether
2N hydrochloric ether: 2N solution of hydrochloric acid in diethyl ether
Iso ether: diisopropyl ether
Mp: melting point
HPLC: high performance liquid chromatography
HPLC: ultraperformance liquid chromatography
MeOH: methanol
Silica H: gel of silica 60 H sold by Merck (DARMSTAD)
Buffer solution pH=2: solution of 16.66 g of $KHSO_4$ and 32.32 g of $K_2SO_4$ in 1 liter of water
AT: ambient temperature
TBTU: O-benzotriazol-1-yl-N,N,N',N'-tetramethyl-uronium tetrafluoroborate
TFA: trifluoroacetic acid
THF: tetrahydrofuran
Tetrakis: tetrakis(triphenylphosphine)palladium The nuclear magnetic resonance spectra are recorded in DMSO-d6. The following abbreviations are used for the interpretation of the spectra: s: singlet, d: doublet, t: triplet, q: quadruplet, qui: quintuplet, m: unresolved peak, bs: broad singlet, sd: split doublet.

The compounds according to the invention are analyzed by coupled LC/UV/MS (liquid chromatography/UV detection/ mass spectrometry). The characteristic molecular peak (MH$^+$) and the retention time (rt) in minutes (min) are measured.

The compounds are analyzed by coupled HPLC-UV-MS or else HPLC-UV-MS (liquid chromatography-UV detection and mass detection).

The analytical conditions are the following:
Conditions A (HPLC):
  A Symmetry C18 (50×2.1 mm; 3.5 μm) column is used.
  Eluent A: 0.005% of TFA in water at approximately pH 3.1
  Eluent B: 0.005% of TFA in acetonitrile.
  Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: λ=210 nm–220 nm
Conditions B (HPLC):
  An XTerra MS C18 (50×2.1 mm; 3.5 μm) column is used.
  Eluent A: 10 mM AcONH$_4$ at approximately pH 7
  Eluent B: acetonitrile
  Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: λ=220 nm
Conditions C (UPLC):
  An Acquity BEH C18 (50×2.1 mm; 1.7 μm) column is used.
  Eluent A: 0.005% of TFA in water at approximately pH 3.1/acetonitrile (97/3)
  Eluent B: 0.035% of TFA in acetonitrile.
  Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Column temperature: 40° C.; flow rate: 1 ml/minute.
Detection: λ=220 nm

Mass Spectrometry Conditions

The mass spectra are recorded in positive electrospray (ESI) mode, in order to observe the ions resulting from the protonation of the compounds analyzed (MH$^+$) or from the formation of adducts with other cations, such as Na$^+$, K$^+$ etc.

PREPARATIONS

1—Preparation of Compounds of Formula (XIII)

Preparation 1.1

Methyl 4-(4-chlorophenyl)-5-(2,4-dichlorophenyl)-3-methoxythiophene-2-carboxylate (XIII):

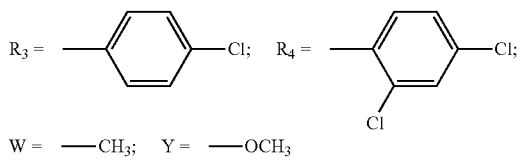

W = —CH$_3$;  Y = —OCH$_3$

A) Methyl 4,5-dibromo-3-methoxythiophene-2-carboxylate 9.97 ml of a solution of iodomethane and then 29.44 g of K$_2$CO$_3$ are added, dropwise, to a solution of 34.35 g of methyl 4,5-dibromo-3-hydroxythiophene-2-carboxylate in 150 ml of DMF and the mixture is left to stir for 18 hours at AT. After cooling, the reaction mixture is diluted in 100 ml of ethyl ether and filtered, and the filtrate is concentrated under vacuum. The reaction crude is purified by silica gel chromatography, elution being carried out with heptane and then with a heptane/EtOAc mixture (85/15; v/v). 28.70 g of the expected compound are obtained.

B) Methyl 4-bromo-5-(2,4-dichlorophenyl)-3-methoxythio-phene-2-carboxylate 16.60 g of (2,4-dichlorophenyl)boronic acid and then, dropwise, 87 ml of a 2M solution of Na$_2$CO$_3$ are added to a solution of 28.70 g of the compound of step A) in 110 ml of toluene. Argon is sparged into the reaction mixture for 30 minutes, 5.03 g of tetrakis are then added and the mixture is heated at 110° C. for 18 hours. After cooling to AT, 80 ml of distilled water are added to the reaction mixture, extraction is carried out with 80 ml of EtOAc, drying is carried out over Na$_2$SO$_4$ and the solvent is evaporated off under vacuum. The reaction crude is purified by silica gel chromatography, elution being carried out with heptane and then with a heptane/EtOAc mixture (85/15; v/v). 16.21 g of the expected compound are obtained.

C) Methyl 4-(4-chlorophenyl)-5-(2,4-dichlorophenyl)-3-methoxythiophene-2-carboxylate 7.75 g of (4-chlorophenyl)boronic acid and then, dropwise, 40.93 ml of a 2M solution of Na$_2$CO$_3$ are added to a solution of 16.21 g of the compound of step B) in 110 ml of toluene. Argon is sparged into the reaction mixture for 30 minutes, then 2.36 g of Tetrakis are added and heating is carried out at 110° C. for 18 hours. After cooling to AT, the reaction mixture is rinsed with 80 ml of distilled water, then extraction is carried out with 80 ml of EtOAc, drying is carried out over Na$_2$SO$_4$, and the solvent is evaporated off under vacuum. The reaction crude is purified by silica gel chromatography, elution being carried out with heptane and then with a heptane/EtOAc mixture (85/15; v/v). 13.23 g of the expected compound are obtained.

Preparation 1.2

Methyl 5-(2-chlorophenyl)-4-(4-chlorophenyl)-3-methoxy-thiophene-2-carboxylate (XIII):

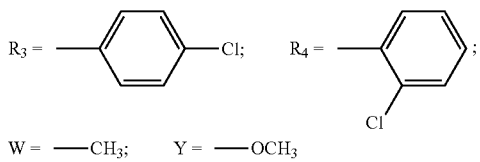

W = —CH$_3$;   Y = —OCH$_3$

A) Methyl 4-bromo-5-(2-chlorophenyl)-3-methoxythiophene-2-carboxylate 11.39 g of compound of step A) of preparation 1.1, 5.56 g of 2-chlorophenylboronic acid and 34.52 ml of a 2M solution of sodium carbonate are added to 60 ml of toluene. Argon is bubbled through for 30 min, before adding 1.99 g of Tetrakis. Heating is carried out at 110° C. overnight. After a return to ambient temperature, 60 ml of distilled water are added and the mixture is extracted with 60 ml of ethyl acetate, and the organic phase is dried and evaporated. The product obtained is purified by silica chromatography (eluent: heptane/ethyl acetate (80/20; v/v)). 7.84 g of the expected compound are obtained.

B) Methyl 5-(2-chlorophenyl)-4-(4-chlorophenyl)-3-methoxythiophene-2-carboxylate 7.84 g of compound of step A, 4.10 g of 4-chlorophenylboronic acid and 21.68 ml of a 2M solution of sodium carbonate are added to 60 ml of toluene. Argon is bubbled through for 30 min, before adding 1.25 g of Tetrakis. Heating is carried out at 110° C. overnight. After a return to ambient temperature, 60 ml of distilled water are added and the mixture is extracted with 60 ml of ethyl acetate, and the organic phase is dried and evaporated. The product obtained is purified by silica chromatography (eluent: heptane/ethyl acetate (80/20; v/v)). 4.90 g of the expected compound are obtained.

2—Preparation of Compounds of Formula (XI)

Preparation 2.1

4-(4-Chlorophenyl)-5-(2,4-dichlorophenyl)-3-methoxythiophene-2-carboxylic acid (XI):

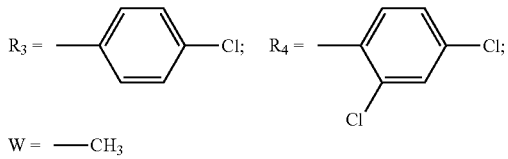

W = —CH$_3$ 1.86 g of NaOH pellets are added to a mixture of 13.23 g of the compound of preparation 1.1 in a 60 ml DMF/MeOH mixture (50/50; v/v) and heating is carried out at 80° C. for 18 hours. The resulting product is evaporated to dryness, the residue is taken up with 30 ml of distilled water, and the aqueous phase is washed with 50 ml of ethyl ether. The aqueous phase is then acidified by adding HCl to pH=2, and filtration by suction and drying are carried out. 12.43 g of the expected compound are obtained.

3. Preparation of Compounds of Formula (IX)

Preparation 3.1

1-{[4-(4-Chlorophenyl)-5-(2,4-dichlorophenyl)-3-methoxythien-2-yl]carbonyl}-4-phenylpiperidine-4-carboxamide (IX):

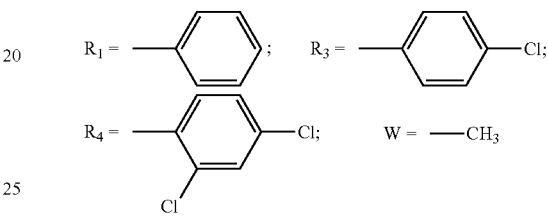

1.16 g of 4-phenylpiperidine-4-carboxamide hydrochloride and then, dropwise, 2.02 ml of a triethylamine solution and 1.71 g of TBTU are added to a mixture of 2 g of the compound of preparation 2.1 in 100 ml of DCM. The mixture is left to stir for 1 hour at ambient temperature. The solvent is evaporated off under vacuum, a buffer solution pH=2 is added, the mixture is extracted with EtOAc and the resulting product is dried, filtered and concentrated. The reaction crude is purified by silica gel chromatography, elution being carried out with DCM and then with a DCM/MeOH mixture (90/10; v/v). 1.96 g of the expected compound are obtained.

Preparation 3.2

4-(Benzylamino)-1-[[4-(4-chlorophenyl)-5-(2,4-dichloro-phenyl)-3-methoxy-2-thienyl]carbonyl]piperidine-4-carboxamide (IX):

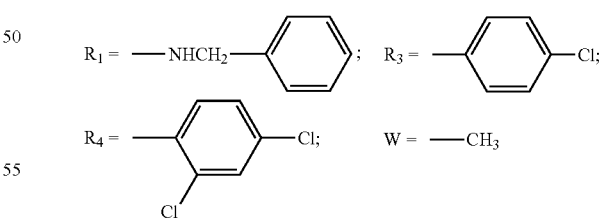

1.34 g of 4-(benzylamino)piperidine-4-carboxamide dihydrochloride, 1.93 ml of triethylamine and 1.4 g of TBTU are added to a mixture of 1.64 g of the compound of preparation 2.1 in 50 ml of DCM, and the mixture is left to stir at ambient temperature for 1 hour. The reaction mixture is concentrated under vacuum, the residue is taken up with a buffer solution pH=2, extraction is carried out with EtOAc, the organic phase is dried over MgSO$_4$, filtration is carried out and the solvent is evaporated off under vacuum. The residue is chromatographed on silica gel, elution being carried out with DCM and then with a DCM/MeOH mixture (60/40; v/v). 2.0 g of the expected compound are obtained.

4—Preparation of Compounds of Formula (II)

Preparation 4.1

1-{[4-(4-Chlorophenyl)-5-(2,4-dichlorophenyl)-3-hydroxythien-2-yl]carbonyl}-4-phenylpiperidine-4-carboxamide

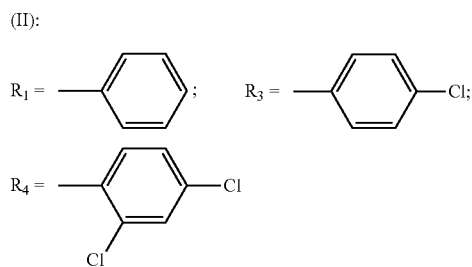

A mixture of 1.81 g of the compound of preparation 3.1 in 20 ml of DCM is cooled to −50° C., and then 9.05 ml of a 1M solution of tribromoborane are added, dropwise, and the temperature is left to return to AT with stirring for 4 hours. The reaction mixture is poured onto ice, the resulting mixture is neutralized to pH=7 by adding concentrated NaOH, extraction is carried out with DCM, and the resulting product is dried and concentrated. The reaction crude is purified by silica gel chromatography, elution being carried out with DCM and then with a DCM/MeOH mixture (97/3; v/v). 0.715 g of the expected compound are obtained.

Preparation 4.2

1-{[4-(4-Chlorophenyl)-5-(2,4-dichlorophenyl)-3-hydroxythien-2-yl]carbonyl}-4-cyclohexylpiperidine-4-carboxamide

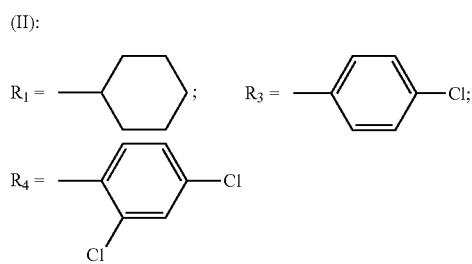

This compound is prepared according to the procedures described in preparations 3.1 and 4.1, using 4-cyclohexylpiperidine-4-carboxamide and the compound of preparation 2.1.

Preparation 4.3

4-(Benzylamino)-1-[[4-(4-chlorophenyl)-5-(2,4-dichloro-phenyl)-3-hydroxy-2-thienyl]carbonyl]piperidine-4-carboxamide

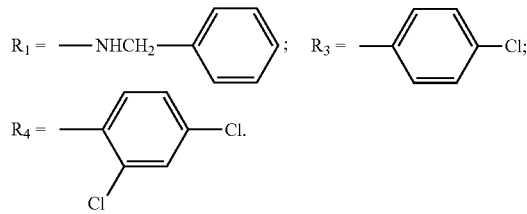

A mixture of 2.0 g of the compound of preparation 3.2 in 40 ml of DCM is cooled to −50° C., and then 9.54 ml of a 1M solution of tribromoborane in DCM are added, dropwise, and the mixture is left to stir for 4 hours while allowing the temperature to return to AT. The reaction mixture is poured onto ice, the resulting mixture is neutralized to pH=7 by adding concentrated NaOH, extraction is carried out with DCM, the organic phase is dried over MgSO₄, filtration is carried out and the solvent is evaporated off under vacuum. The residue is taken up in iso ether, and the precipitate formed is filtered off by suction and dried under vacuum. 1.92 g of the expected compound are obtained.

5—Preparation of Compounds of Formula (XII)

Preparation 5.1

Methyl 5-(2-chlorophenyl)-4-(4-chlorophenyl)-3-hydroxy-thiophene-2-carboxylate

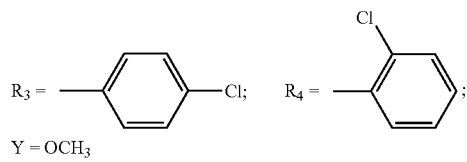

3.35 g of the compound of preparation 1.2 are added to 20 ml of DCM, then the mixture is cooled to −50° C., 6.40 ml of BBr3 (1M in DCM) are added dropwise, and then the mixture is allowed to return to ambient temperature. The mixture is concentrated, the resulting product is taken up with DCM, washing is carried out with 50 ml of water, drying is carried out, and the resulting product is concentrated. The product obtained is purified by silica chromatography (eluent: heptane/ethyl acetate (80/20; v/v)). 2.47 g of the expected compound are obtained.

6. Preparation of Compounds of Formula (X)

Preparation 6.1

Methyl 5-(2-chlorophenyl)-4-(4-chlorophenyl)-3-[3-(tetrahydro-2H-pyran-2-yloxy)propoxy]thiophene-2-carboxylate

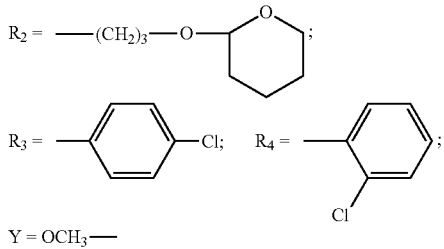

(X):

$R_2 = $ —(CH$_2$)$_3$—O—

$R_3 = $ —C$_6$H$_4$—Cl;  $R_4 = $ —C$_6$H$_4$—Cl;

Y = OCH$_3$—

0.7 g of the compound of preparation 5.1, 0.824 g of 2-(3-bromopropoxy)tetrahydro-2H-pyran and 1.2 g of Cs$_2$CO$_3$ are added to 20 ml of acetone and the mixture is refluxed overnight. Filtration is carried out and the resulting product is concentrated. The product obtained is purified by silica chromatography (eluent: heptane/ethyl acetate (60/40; v/v)). 0.950 g of the expected compound is obtained.

7. Preparation of Compounds of Formula (IV)

Preparation 7.1

5-(2-Chlorophenyl)-4-(4-chlorophenyl)-3-[3-(tetrahydro-2H-pyran-2-yloxy)propoxy]thiophene-2-carboxylic acid (IV):

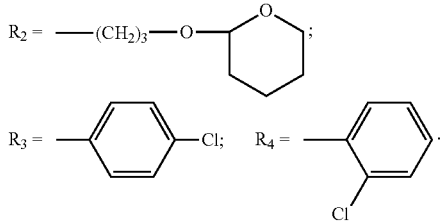

$R_2 = $ —(CH$_2$)$_3$—O—

$R_3 = $ —C$_6$H$_4$—Cl;  $R_4 = $ —C$_6$H$_4$—Cl.

A mixture of 0.95 g of the compound of preparation 6.1 and 0.29 g of NaOH pellets in 40 ml of MeOH and 1 ml of water is refluxed for 3 hours. The reaction mixture is concentrated under vacuum, the residue is taken up in a buffer solution pH=2, extraction is carried out with DCM, the organic phase is dried over MgSO$_4$, filtration is carried out and the solvent is evaporated off under vacuum. The residue is chromatographed on silica gel, elution being carried out with DCM and then a gradient of the mixture DCM/MeOH up to (80/40; v/v). 0.564 g of the expected compound is obtained.

8—Preparation of Compounds of Formula (V)

Preparation 8.1

4-[(3,3,3-Trifluoropropyl)amino]-4-piperidinecarboxamide $R_1 = $ —NH(CH$_2$)$_2$—CF$_3$  (V)

A) tert-Butyl 4-carbamoyl-4-[(3,3,3-trifluoropropyl)-amino]piperidine-1-carboxylate 10 g of tert-butyl 4-amino-4-carbamoylpiperidine-1-carboxylate, 4.42 g of 3,3,3-trifluoropropionaldehyde, 17.61 g of sodium triacetoxyborohydride and 4.51 ml of acetic acid are added, at AT, to 250 ml of DCM, and then the mixture is stirred for 3 hours. Water is added and the expected compound is extracted with DCM, and the organic phase is washed with a saturated solution of NaHCO$_3$ and then with water. After drying of the organic phase, filtration and evaporation to dryness, 13 g of expected compound are obtained.

B) 4-[(3,3,3-Trifluoropropyl)amino]piperidine-4-carboxamide 13 g of compound obtained in (A) are stirred into 25 ml of MeOH, then 30 ml of hydrochloric ether (2M) are added and the mixture is left to stir overnight. After filtration and drying, 9.57 g of expected compound are obtained.

Preparation 8.2

4-Phenylpiperidine-4-carboxamide hydrochloride (V):

$R_1 = $ 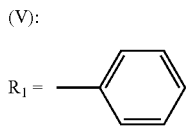

A) 1-Benzyl-4-phenylpiperidine-4-carboxamide hydrochloride 10 g of 1-benzyl-4-phenylpiperidine-4-carbonitrile are added to 77 ml of concentrated sulfuric acid and then the mixture is heated at 100° C. for one hour. The reaction mixture is then added to ice and then basified with NH$_4$OH. The product is extracted with CH$_2$Cl$_2$, dried and evaporated. After crystallization of the hydrochloride from ether, 5.7 g of expected product are obtained.

B) 4-Phenylpiperidine-4-carboxamide hydrochloride 5.6 g of product obtained in (A), 6.7 g of cyclohexadiene and 0.5 g of palladium-on-carbon (10%) are added to 70 ml of MeOH and the reaction mixture is refluxed for 6 hours. The catalyst is filtered off over celite and the resulting product is evaporated to dryness. After crystallization from an ether-isopropyl ether mixture, 3 g of expected product are obtained.

EXAMPLES

Example 1
Compound No. 6

1-{[4-(4-Chlorophenyl)-5-(2,4-dichlorophenyl)-3-(2-hydroxyethoxy)thien-2-yl]carbonyl}-4-phenylpiperidine-4-carboxamide A) 1-({4-(4-Chlorophenyl)-5-(2,4-dichlorophenyl)-3-[2-(tetrahydro-2H-pyran-2-yloxy)ethoxy]thien-2-yl}carbonyl)-4-phenylpiperidine-4-carboxamide 0.188 g of 2-(2-bromoethoxy)tetrahydro-2H-pyran and 0.294 g of $Cs_2CO_3$ are added to a mixture of 0.264 g of the compound of preparation 4.1 in 20 ml of acetone. The mixture is refluxed for 18 hours. Filtration is carried out and the filtrate is concentrated under vacuum. The reaction crude is purified by silica gel chromatography, elution being carried out with DCM and then with a DCM/MeOH mixture (97/3; v/v). 0.272 g of the expected compound is obtained.

B) 1-{[4-(4-Chlorophenyl)-5-(2,4-dichlorophenyl)-3-(2-hydroxyethoxy)thien-2-yl]carbonyl}-4-phenylpiperidine-4-carboxamide Amberlyst 15 resin is added to a mixture of 0.272 g of the compound of the preceding step in 15 ml of acetone, and then the mixture is refluxed for 2 hours. Filtration and concentration are carried out. The reaction crude is purified by silica gel chromatography, elution being carried out with DCM and then with a DCM/MeOH mixture (97/3; v/v). 0.146 g of the expected compound is obtained.

Example 2
Compound No. 4

1-{[4-(4-Chlorophenyl)-5-(2,4-dichlorophenyl)-3-(3-hydroxypropoxy)thien-2-yl]carbonyl}-4-phenylpiperidine-4-carboxamide This compound is prepared according to a procedure similar to that described in steps A) and B) described in example 1, using the compound of preparation 4.1 and 2-(3-bromopropoxy)tetrahydro-2H-pyran.

Example 3
Compound No. 5

1-({4-(4-Chlorophenyl)-5-(2,4-dichlorophenyl)-3-[3-(methylsulfonyl)propoxy]thien-2-yl}carbonyl)-4-phenylpiperidine-4-carboxamide 0.148 g of 3-(methylsulfonyl)propylmethanesulfonate and 0.294 g of $Cs_2CO_3$ are added to a mixture of 0.200 g of the compound of preparation 4.1 in 15 ml of acetone. The mixture is refluxed for 18 hours. Filtration by suction and concentration are carried out. The reaction crude is purified by silica gel chromatography, elution being carried out with DCM and then with a DCM/MeOH mixture (97/3; v/v). 0.065 mg of the expected compound is obtained.

Example 4
Compound No. 2

1'-{[4-(4-Chlorophenyl)-5-(2,4-dichlorophenyl)-3-{(3-[(methylsulfonyl)amino]propoxy}thien-2-yl]carbonyl}-4-cyclohexylpiperidine-4-carboxamide A) tert-Butyl [3-({2-[(4-carbamoyl-4-cyclohexylpiperidin-1-yl)carbonyl]-4-(4-chlorophenyl)-5-(2,4-dichlorophenyl)thien-3-yl}oxy)propyl]carbamate 0.212 g of tert-butyl (3-bromopropyl)carbamate and 0.290 g of $Cs_2CO_3$ are added to a mixture of 0.300 g of the compound of preparation 4.2 in 20 ml of acetone. The mixture is refluxed for 18 hours. Filtration by suction and concentration are carried out. 0.291 g of the expected compound is obtained.

B) 1-{[3-(3-Aminopropoxy)-4-(4-chlorophenyl)-5-(2,4-dichlorophenyl)thien-2-yl]carbonyl}-4-cyclohexyl-piperidine-4-carboxamide 5 ml of a 2M solution of hydrochloric ether are added, dropwise, to a mixture of 0.291 g of the compound of the preceding step in 15 ml of DCM. The mixture is left to stir overnight at AT. The reaction mixture is concentrated to dryness, and the residue is taken up in ethyl ether, filtered by suction and dried. 0.257 g of the expected compound is obtained.

C) 1-{[4-(4-Chlorophenyl)-5-(2,4-dichlorophenyl)-3-{3-[(methylsulfonyl)amino]propoxy}thien-2-yl]carbonyl}-4-cyclohexylpiperidine-4-carboxamide 0.04 ml of a methanesulfonyl chloride solution and 0.18 ml of a triethylamine solution are added, dropwise, to a mixture of 0.257 mg of the compound of the preceding step in 10 ml of DCM, and the mixture is left to stir at AT for 1 hour. The reaction mixture is evaporated to dryness, washing is carried out with 15 ml of distilled water, extraction is carried out with DCM, and drying and concentration are carried out. 0.198 g of the expected compound is obtained.

Example 5
Compound No. 24

4-(Benzylamino)-1-[[4-(4-chlorophenyl)-5-(2,4-dichloro-phenyl)-3-(3-hydroxypropyl)-2-thienyl]carbonyl]-piperidine-4-carboxamide hydrochloride A) 4-(Benzylamino)-1-[[4-(4-chlorophenyl)-5-(2,4-dichlorophenyl)-3-[3-(tetrahydro-2H-pyran-2-yloxy)propoxy]-2-thienyl]carbonyl]piperidine-4-carboxamide A mixture of 0.35 g of the compound of preparation 4.3, 0.153 g of 2-(3-bromopropoxy)tetrahydro-2H-pyran and 0.22 g of $Cs_2CO_3$ in 15 ml of acetone is refluxed overnight. The reaction mixture is filtered and the filtrate is concentrated under vacuum. The residue is chromatographed on silica gel, elution being carried out with DCM and then with a gradient of the mixture DCM/MeOH up to (75/25; v/v). 0.3 g of the expected compound is obtained.

B) 4-(Benzylamino)-1-[[4-(4-chlorophenyl)-5-(2,4-dichlorophenyl)-3-(3-hydroxypropoxy)-2-thienyl]-carbonyl]piperidine-4-carboxamide hydrochloride 30 ml of a 2N hydrochloric ether solution are added to a mixture of 0.3 g of the compound of the preceding step in 15 ml of MeOH, and the mixture is left to stir for 1 hour at AT. The reaction mixture is concentrated under vacuum and the residue is chromatographed on silica gel, elution being carried out with a mixture of $MeOH/H_2O$ from (65/35; v/v) to (90/10; v/v). 0.18 g of the expected compound is obtained after crystallization from iso ether.

Example 6
Compound No. 26

1-[5-(2-Chlorophenyl)-4-(4-chlorophenyl)-3-[3-(hydroxypropoxy)-2-thienyl]carbonyl]-4-[(4-fluorobenzyl)amino]piperidine-4-carboxamide hydrochloride A) 1-[[5-(2-Chlorophenyl)-4-(4-chlorophenyl)-3-[3-(tetrahydro-2H-pyran-2-yloxy)propoxy]-2-thienyl]-carbonyl]-4-[(4-fluorobenzyl)amino]piperidine-4-carboxamide A mixture of 0.3 g of the compound of preparation 7.1, 0.19 g of 4-[(4-fluorobenzyl)amino]piperidine-4-carboxamide dihydrochloride, 0.29 ml of triethylamine and 0.19 g of TBTU in 20 ml of DCM is left to stir for 1 hour at AT. The reaction mixture is concentrated under vacuum, the residue is taken up in 70 ml of buffer pH=2, extraction is carried out with DCM, the organic phase is dried over $MgSO_4$, filtration is carried out and the solvent is evaporated off under vacuum. The residue is chromatographed on silica gel, elution being carried out with DCM and then with a gradient of the mixture DCM/MeOH up to (70/30; v/v). 0.35 g of the expected product is obtained.

B) 1-[5-(2-Chlorophenyl)-4-(4-chlorophenyl)-3-[3-(hydroxypropoxy)-2-thienyl]carbonyl]-4-[(4-fluorobenzyl)amino]piperidine-4-carboxamide hydrochloride 30 ml of a 2N hydrochloric ether solution are added to a mixture of 0.35 g of the compound of the preceding step in 30 ml of MeOH, and the mixture is left to stir overnight at AT. The reaction mixture is concentrated under vacuum and the residue is chromatographed on silica gel, elution being carried out with the mixture DCM/MeOH up to (60/40; v/v). 0.186 g of the expected compound is obtained after crystallization from iso ether.

Example 7
Compound No. 27

1-[5-(2-Chlorophenyl)-4-(4-chlorophenyl)-3-[3-(hydroxypropoxy)-2-thienyl]carbonyl]-4-phenyl-piperidine-4-carboxamide A) 1-[5-(2-Chlorophenyl)-4-(4-chlorophenyl)-3-[3-(tetrahydro-2H-pyran-2-yloxy)thienyl]carbonyl]-4-phenylpiperidine-4-carboxamide A mixture of 0.26 g of the compound of preparation 7.1, 0.13 g of 4-phenylpiperidine-4-carboxamide hydrochloride, 0.21 ml of triethylamine and 0.165 g of TBTU in 20 ml of DCM is left to stir for 1 hour at AT. The reaction mixture is concentrated under vacuum, the residue is taken up in 70 ml of buffer pH=2, extraction is carried out with DCM, the organic phase is dried over $MgSO_4$, filtration is carried out and the solvent is evaporated off under vacuum. The residue is chromatographed on silica gel, elution being carried out with DCM and then with a gradient of the mixture DCM/MeOH up to (60/40; v/v). 0.2 g of the expected compound is obtained.

B) 1-{[5-(2-Chlorophenyl)-4-(4-chlorophenyl)-3-(3-hydroxypropoxy)-2-thienyl]carbonyl}-4-phenylpiperidine-4-carboxamide A mixture of 0.2 g of the compound of the preceding step and of the Amberlyst 15 resin in 30 ml of MeOH is refluxed overnight. The reaction mixture is filtered and the filtrate is concentrated under vacuum. The residue is chromatographed on silica gel, elution being carried out with DCM and then with a gradient of the mixture DCM/MeOH up to (60/40; v/v). 0.1 g of the expected compound is obtained.

Tables 1 and 2 indicate the chemical structures of some compounds according to the invention and also their physicochemical properties (analysis by coupled LC/UV/MS: liquid chromatography/UV detection/mass spectrometry). These compounds are exemplified above or prepared according to procedures similar to those of the exemplified compounds (Examples 1 to 35).

In these tables, Me represents a methyl group.

TABLE 1

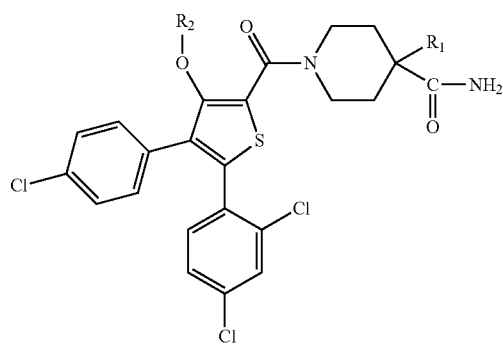

(I)

| Compound No. | $R_1$ | $R_2$ | Characterization LC/MS $MH^+$; rt (min)(condition) |
|---|---|---|---|
| 1 | —N(piperidine) | —Me | $MH^+$ = 605 rt = 7.99 (A) |
| 2 | —N(piperidine) | —$(CH_2)_3$—NH—$SO_2$—Me | $MH^+$ = 726 rt = 7.8 (A) |
| 3 | —N(piperidine) | —$(CH_2)_3$—$SO_2$Me | $MH^+$ = 711 rt = 7.81 (A) |

TABLE 1-continued (I)

[Structure: thiophene core with R₂-O substituent, 4-chlorophenyl group, 2,4-dichlorophenyl group, linked via carbonyl to a piperidine bearing R₁ and C(O)NH₂ substituents]

| Compound No. | R₁ | R₂ | Characterization LC/MS MH⁺; rt (min)(condition) |
|---|---|---|---|
| 4 | phenyl | —(CH$_2$)$_3$—OH | MH⁺ = 642<br>rt = 10.5<br>(A) |
| 5 | phenyl | —(CH$_2$)$_3$—SO$_2$—Me | MH⁺ = 704<br>rt = 10.5<br>(A) |
| 6 | phenyl | —(CH$_2$)$_2$—OH | MH⁺ = 628<br>rt = 10.43<br>(A) |
| 7 | N-methyl-4,4-difluoropiperidinyl | —(CH$_2$)$_2$—OH | MH⁺ = 671<br>rt = 1.74<br>(C) |
| 8 | N-methyl-4,4-difluoropiperidinyl | —(CH$_2$)$_3$—SO$_2$Me | MH⁺ = 747<br>rt = 1.79<br>(C) |
| 9 | N-methyl-4,4-difluoropiperidinyl | —(CH$_2$)$_3$—OH | MH⁺ = 685<br>rt = 1.78<br>(C) |
| 10 | —HN—(CH$_2$)$_2$—CF$_3$ | —(CH$_2$)$_2$—OH | MH⁺ = 663<br>rt = 9.86<br>(B) |
| 11 | —HN—(CH$_2$)$_2$—CF$_3$ | —(CH$_2$)$_3$—SO$_2$Me | MH⁺ = 739<br>rt = 1.6<br>(C) |
| 12 | —HN—(CH$_2$)$_2$—CF$_3$ | —(CH$_2$)$_2$—NH—CO—CH$_2$OH | MH⁺ = 720<br>rt = 1.48<br>(C) |
| 13 | —HN—(CH$_2$)$_2$—CF$_3$ | —(CH$_2$)$_3$—OH | MH⁺ = 677<br>rt = 10.14<br>(B) |
| 14 | phenyl | —(CH$_2$)$_2$—NH—CO—CH$_2$OH | MH⁺ = 685<br>rt = 9.95<br>(A) |
| 15 | phenyl | —(CH$_2$)$_2$—NH—CO—Me | MH⁺ = 659<br>rt = 1.81<br>(C) |

TABLE 1-continued
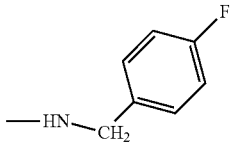
(I)
| Compound No. | R₁ | R₂ | Characterization LC/MS MH⁺; rt (min)(condition) |
|---|---|---|---|
| 16 | 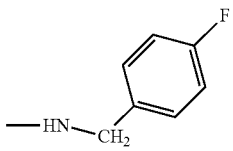 | —(CH₂)₂—OH | MH⁺ = 675<br>rt = 1.56<br>(C) |
| 17 | 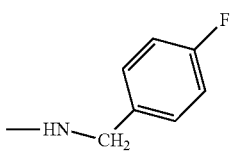 | —(CH₂)₃—OH | MH⁺ = 689<br>rt = 1.58<br>(C) |
| 18 | 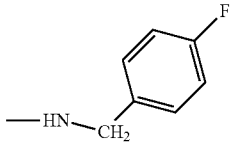 | —(CH₂)₃—SO₂—Me | MH⁺ = 751<br>rt = 1.57<br>(C) |
| 19 | 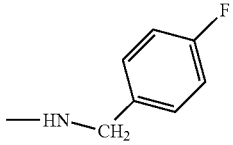 | —(CH₂)₂—NH—CO—Me | MH⁺ = 716<br>rt = 1.53<br>(C) |
| 20 | 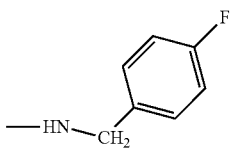 | —(CH₂)₂—NH—CO—CH₂OH | MH⁺ = 732<br>rt = 1.48<br>(C) |
| 21 | 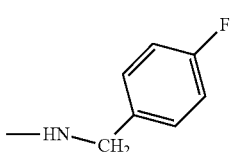 | —(CH₂)₃—NH—CO—CH₂OH | MH⁺ = 746<br>rt = 1.53<br>(C) |
| 22 |  | —(CH₂)₃—NH—CO—Me | MH⁺ = 730<br>rt = 1.59<br>(C) |

TABLE 1-continued (I)

| Compound No. | R₁ | R₂ | Characterization LC/MS MH⁺; rt (min)(condition) |
|---|---|---|---|
| 23 | —HN—CH₂—(phenyl) | —(CH₂)₂—OH | MH⁺ = 557<br>rt = 1.55<br>(C) |
| 24 | —HN—CH₂—(phenyl) | —(CH₂)₃—OH | MH⁺ = 671<br>rt = 1.56<br>(C) |
| 25 | —HN—CH₂—(phenyl) | —(CH₂)₂—NH—CO—CH₂OH | MH⁺ = 714<br>rt = 1.46<br>(C) |

TABLE 2

(I)

| Compound No. | R₁ | R₂ | Salt | Characterization LC/MS MH⁺; rt (min)(condition) |
|---|---|---|---|---|
| 26 | —NH—CH₂—(4-F-phenyl) | —(CH₂)₃—OH | HCl | MH⁺ = 655<br>rt = 1.43<br>(C) |
| 27 | —(4-methylphenyl) | —(CH₂)₃—OH | — | MH⁺ = 608<br>rt = 1.72<br>(C) |

TABLE 2-continued (I)

[Structure: thiophene core with R2-O- group, carbonyl linked to piperidine bearing R1 and C(O)NH2 groups; thiophene also substituted with 4-chlorophenyl and 2-chlorophenyl groups]

| Compound No. | R₁ | R₂ | Salt | Characterization LC/MS MH⁺; rt (min)(condition) |
|---|---|---|---|---|
| 28 | [phenyl] | —(CH₂)₂—OH | — | MH⁺ = 594<br>rt = 1.7<br>(C) |
| 29 | —NH—CH₂—[phenyl]—F | —(CH₂)₂—OH | HCl | MH⁺ = 641<br>rt = 1.41<br>(C) |
| 30 | —NH—CH₂—[phenyl]—F | —(CH₂)₂—NH₂ | HCl | MH⁺ = 640<br>rt = 1.18<br>(C) |
| 31 | —NH—CH₂—[phenyl]—F | —(CH₂)₂—NHCOCH₃ | — | MH⁺ = 682<br>rt = 1.38<br>(C) |
| 32 | [phenyl] | —(CH₂)₂—NH₂ | HCl | MH⁺ = 593<br>rt = 8.42<br>(B) |
| 33 | [phenyl] | —(CH₂)₂—NHCOCH₂OH | — | MH⁺ = 651<br>rt = 8.79<br>(B) |
| 34 | [phenyl] | —(CH₂)₂—NHCOCH₃ | — | MH⁺ = 635<br>rt = 1.64<br>(C) |
| 35 | —NH—CH₂—[phenyl]—F | —(CH₂)₂—NHCOCH₂OH | — | MH⁺ = 699<br>rt = 1.33<br>(C) |

The analyses carried out by NMR for compounds 24, 26 and 27 are given hereinafter:

Compound 24: $^1$H NMR: DMSO-d$_6$ (250 MHz): δ (ppm): 1.53-1.68: m: 2H, 1.68-2.01: m: 4H, 3.25-3.34: m: 4H, 3.42-3.98: m: 4H, 3.87: t: 2H, 4.34: t: 1H, 7.10-7.21: m: 3H, 7.22-7.51: m: 11H, 7.68: d: 1H.

Compound 26: $^1$H NMR: DMSO-d$_6$ (250 MHz): δ (ppm): 1.54-1.68: m: 2H, 1.68-2.19: m: 2H, 2.33-2.58: m: 2H, 3.20-3.40: m: 4H, 3.44-3.71: m: 2H, 3.87: t: 2H, 3.95-4.22: m: 2H, 4.39: bs: 1H, 7.17: d: 3H, 7.22-7.54: m: 9H, 7.65: bs: 1H, 8.06: bs: 1H, 9.62: bs: 1H.

Compound 27: $^1$H NMR: DMSO-d$_6$ (250 MHz): δ (ppm): 1.46-1.65: m: 2H, 1.74-1.96: m: 2H, 2.50-2.63: m: 2H, 3.25: bs: 2H, 3.21-3.30: m: 2H, 3.85: t: 2H, 4.7: bs: 2H, 4.35: t: 1H, 7.11: s: 1H, 7.17: d: 2H, 7.22-7.32: m: 2H, 7.32-7.57: m: 10H.

The compounds of formula (I) have a very good affinity in vitro (IC$_{50}$ ≤ 10$^{-7}$ M) for cannabinoid CB$_1$ receptors, under the experimental conditions described by M. Rinaldi-Carmona et al. (FEBS Letters, 1994, 350, 240-244).

The antagonist nature of the compounds of formula (I) was demonstrated, in vitro, by the results obtained in adenylate cyclase inhibition models as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The weak penetration of the compounds of formula (I) across the blood-brain barrier (BBB) was evaluated in vivo by:

measurement (1): quantification of the compounds of formula (I) (unchanged) in samples of mouse brain after intravenous or oral administration, by means of an analytical technique (LC-MS/MS). The ratio $$\frac{\text{amount present in the brain}}{\text{amount present in the plasma}}$$

of less than 0.2 reflects a weak penetration of the compound into the brain.

measurement (2): measurement of the interaction of the compounds of formula (I) with the CB1 receptors present in the brain in mice by means of a test for ex vivo binding of [3H]-CP55940 (CB1 agonist) after intravenous administration (10 mg/kg) as described in M. Rinaldi-Carmona et al., FEBS Letters, 1994, 350, 240-244 and M. Rinaldi-Carmona et al., Life Sciences, 1995, 56, 1941-1947, M. Rinaldi-Carmona et al., J. Pharmacol. Exp. Ther., 2004, 310, 905-914.

A percentage inhibition of [3H]-CP55940 binding in the brain of less than 50% at 10 mg/kg reflects a weak penetration into the brain. Preferably, this percentage is less than 40% and more preferentially less than 30%.

measurement (3): measurement of the blocking, by the compounds of formula (I), of the hypothermic effect induced by a CB1 receptor agonist (CP55940), after intravenous administration, as described in Rinaldi-Carmona M. et al., JPET 2004, 310, 905-914.

A percentage reversion of the effect of CP55940 of less than 50% at 10 mg/kg reflects a weak penetration into the brain. Preferably, this percentage is less than 40% and more preferentially less than 30%.

The interaction of the compounds of formula (I) according to the invention with the CB1 receptors present at the periphery was demonstrated in mice by measuring the blocking of the inhibitory effect induced by a CB1 receptor agonist (CP55940) on gastrointestinal transit, after oral administration, as described in M, Rinaldi-Carmona et al., J. Pharmacol. Exp. Ther., 2004, 310, 905-914. A percentage reversion of the effect of CP55940 of greater than 50% at 10 mg/kg reflects a significant antagonist capacity at the level of the CB1 receptors present in the periphery. Preferably, the percentage reversion is between 70% and 100%.

The compounds of formula (I) are compatible with their use as a medicament.

Thus, according to another aspect of the invention, the subject thereof is medicaments for human or veterinary medicine, which comprise a compound of formula (I), or an addition salt of the latter with a pharmaceutically acceptable acid.

Thus, the compounds according to the invention can be used in humans or in animals (in particular in mammals, including, in a nonlimiting manner, dogs, cats, horses, cattle, sheep) in the treatment or prevention of diseases involving cannabinoid $CB_1$ receptors.

For example, and in a nonlimiting manner, the compounds of formula (I) are of use as psychotropic medicaments, in particular for the treatment of psychiatric disorders including anxiety, depression, mood disorders, insomnia, delirious conditions, obsessive disorders, psychoses in general, schizophrenia, attention deficit hyperactivity disorders (ADHD) in hyperkinetic children, and also for the treatment of disorders related to the use of psychotropic substances, in particular in the case of a substance abuse and/or a substance dependence, including alcohol dependence and nicotine dependence.

The compounds of formula (I) according to the invention can be used as medicaments for the treatment of migraine, stress, diseases of psychosomatic origin, panic attacks, epilepsy, motor disorders, in particular dyskinesia or Parkinson's disease, shaking and dystonia.

The compounds of formula (I) according to the invention can also be used as medicaments in the treatment of memory disorders, cognitive disorders, in particular in the treatment of senile dementia and Alzheimer's disease, and also in the treatment of attention or consciousness disorders.

Furthermore, the compounds of formula (I) may be used as neuroprotective agents, in the treatment of ischemia and cranial trauma and the treatment of acute or chronic neurodegenerative diseases, including chorea, Huntington's chorea and Tourette's syndrome.

The compounds of formula (I) according to the invention can be used as medicaments in the treatment of pain: neuropathic pain, acute peripheral pain, chronic pain of inflammatory origin, pain induced by an anticancer treatment.

The compounds of formula (I) according to the invention can be used as medicaments in human or veterinary medicine in the prevention and treatment of appetite disorders, appetence disorders (appetence for sugars, carbohydrates, drugs, alcohol or any appetizing substance) and/or eating behavior disorders, in particular for the treatment of obesity or bulimia and also for the treatment of type II diabetes or non-insulin-dependent diabetes and for the treatment of dyslipidemia and metabolic syndrome. Thus, the compounds of formula (I) according to the invention are of use in the treatment of obesity and the risks associated with obesity, in particular the cardiovascular risks.

Furthermore, the compounds of formula (I) according to the invention can be used as medicaments in the treatment and prevention of gastrointestinal disorders, diarrhea disorders, ulcers, vomiting, bladder and urinary disorders, liver diseases which may or may not be of alcoholic origin, such as chronic cirrhosis, fibrosis, hepatic steatosis or steatohepatitis; and also disorders of endocrine origin, cardiovascular disorders, hypotension, atherosclerosis, hemorrhagic shock, septic shock, asthma, chronic bronchitis, chronic obstructive pulmonary disorders, Raynaud's syndrome, glaucoma, fertility disorders, premature birth, interruption of pregnancy, inflammatory phenomena, immune system diseases, in particular autoimmune and neuroinflammatory diseases such as rheumatoid arthritis, reaction arthritis, diseases resulting in demyelination, multiple sclerosis, infectious and viral diseases such as encephalitis, cerebral strokes, and also as medicaments for anticancer chemotherapy, for the treatment of Guillain-Barré syndrome and for the treatment of bone diseases and osteoporosis. Furthermore, the compounds of formula (I) according to the invention can be used for their protective effects against drug-induced cardiotoxicity.

According to the present invention, the compounds of formula (I) are most particularly of use for the preparation of medicaments of use in the prevention and treatment of psychiatric disorders, in particular schizophrenia, attention and consciousness disorders, attention deficit hyperactivity disorders (ADHD) in hyperkinetic children; in the prevention and treatment of memory deficiencies and cognitive disorders; of dependence on and withdrawal from a substance, in particular alcohol dependence, nicotine dependence, alcohol withdrawal and tobacco withdrawal; acute or chronic neurodegenerative diseases.

More particularly, the compounds of formula (I) according to the present invention are of use for the preparation of medicaments of use in the treatment and prevention of appetite disorders, appetence disorders, metabolic disorders, obesity, type II diabetes, metabolic syndrome, dyslipidemia, gastrointestinal disorders, inflammatory phenomena, immune system diseases, psychotic disorders, alcohol dependence and nicotine dependence.

According to one of its aspects, the present invention relates to the use of a compound of formula (I), or of pharmaceutically acceptable salts thereof, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or the salt thereof, can be administered in a unit administration form, as a mixture with conventional pharmaceutical excipients, to animals and to human beings for the prophylaxis or the treatment of the above disorders or diseases.

The appropriate unit administration forms include forms for oral administration, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

Compound according to the invention: 50.0 mg

Mannitol: 223.75 mg

Sodium croscarmellose: 6.0 mg

Corn starch: 15.0 mg

Hydroxypropylmethylcellulose: 2.25 mg

Magnesium stearate: 3.0 mg

Via oral administration, the dose of active ingredient administered per day can reach 0.01 to 100 mg/kg, taken in one or more intakes, preferentially 0.02 to 50 mg/kg.

There may be specific cases where higher or lower dosages are appropriate; such dosages do not depart from the context of the invention. According to the usual practice, the dosage suitable for each patient is determined by the physician according to the method of administration and the weight and response of said patient.

According to another of its aspects, the present invention also relates to a method for treating the pathological conditions indicated above, which comprises the administration, to a patient, of an effective dose of a compound according to the invention, or a pharmaceutically acceptable salt thereof.

The invention claimed is:

1. A compound of formula (I):

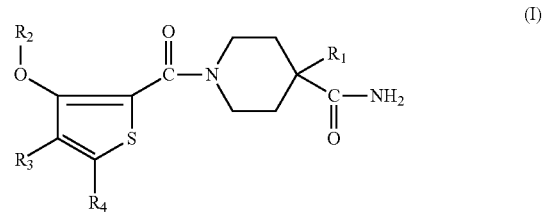

in which:
$R_1$ represents:
an —$NR_5R_6$ group;
a phenyl which is unsubstituted or substituted one or more times with substituents chosen independently from a halogen atom, a ($C_1$-$C_4$)alkyl, a ($C_1$-$C_4$)alkoxy and a trifluoromethyl;
$R_2$ represents:
a ($C_1$-$C_4$)alkyl;
an —X—$R_7$ group;
$R_3$ and $R_4$ each independently represent a phenyl substituted one or more times with a substituent chosen independently from a halogen atom, a ($C_1$-$C_4$)alkyl, a ($C_1$-$C_4$)alkoxy and a trifluoromethyl;
$R_5$ represents a hydrogen atom or a ($C_1$-$C_4$)alkyl;
$R_6$ represents a ($C_1$-$C_4$)alkyl which is unsubstituted or substituted with one or more fluorine atoms or with a phenyl which is unsubstituted or substituted with a halogen atom;
or else $R_5$ and $R_6$, together with the nitrogen atom to which they are bonded, constitute a heterocycle chosen from: azetidine, pyrrolidine, and piperidine, said heterocycle being unsubstituted or substituted one or more times with a halogen atom;
X represents a ($C_1$-$C_5$)alkylene;
$R_7$ represents an —$OR_8$ group, an —$NR_9R_{10}$ group or an —$SO_2$—($C_1$-$C_4$)alkyl group;
$R_8$ represents a hydrogen atom or a ($C_1$-$C_4$)alkyl;
$R_9$ represents a hydrogen atom or a ($C_1$-$C_4$)alkyl;
$R_{10}$ represents a hydrogen atom, a —$COR_{11}$ group, an —$SO_2R_{11}$ group or a —$CO(CH_2)_m OH$ group;
$R_{11}$ represents a ($C_1$-$C_4$)alkyl which is unsubstituted or substituted with one or more fluorine atoms;
m represents 1, 2 or 3;
in the form of a base or of an addition salt with an acid.

2. The compound of formula (I), as claimed in claim 1, in which:
$R_1$ represents:
an —$NR_5R_6$ group;
a phenyl;
$R_2$ represents:
a methyl;
an —X—$R_7$ group;
$R_3$ and $R_4$ each independently represent a phenyl substituted once or twice with a halogen atom;
$R_5$ represents a hydrogen atom;
$R_6$ represents a ($C_1$-$C_4$)alkyl substituted with one or more fluorine atoms or with a phenyl which is unsubstituted or substituted with a halogen atom;
or else $R_5$ and $R_6$, together with the nitrogen atom to which they are bonded, constitute a piperidin-1-yl radical which is unsubstituted or substituted once or twice with a halogen atom;

X represents a $(C_1-C_3)$alkylene;
R$_7$ represents an —OR$_8$ group, an —NR$_9$R$_{10}$ group or an —SO$_2$—CH$_3$ group;
R$_8$ represents a hydrogen atom;
R$_9$ represents a hydrogen atom;
R$_{10}$ represents a hydrogen atom, a —CO—CH$_3$ group, an —SO$_2$—CH$_3$ group or a —COCH$_2$OH group;
in the form of a base or of an addition salt with an acid.

3. The compound of formula (I), as claimed in claim 1, in which:
R$_1$ represents:
an —NH(CH$_2$)$_2$—CF$_3$ group, a 4-fluorobenzylamino group, a benzylamino group, a piperidin-1-yl radical, a 4,4-difluoropiperidin-1-yl radical;
a phenyl;
R$_2$ represents:
a methyl;
an —X—R$_7$ group;
R$_3$ represents a 4-chlorophenyl;
R$_4$ represents a 2-chlorophenyl or a 2,4-dichlorophenyl;
X represents a methylene, an ethylene or a trimethylene;
R$_7$ represents an —OH radical, an —NH$_2$ radical, an —NHCOCH$_3$ group, an —NHSO$_2$CH$_3$ group, an —NHCOCH$_2$OH group or an —SO$_2$—CH$_3$ group;
in the form of a base or of an addition salt with an acid.

4. The compound as claimed in claim 1, chosen from:
1'-{[4-(4-chlorophenyl)-5-(2,4-dichlorophenyl)-3-methoxythien-2-yl]carbonyl}-1,4'-bipiperidine-4'-carboxamide;
1'-{[4-(4-chlorophenyl)-5-(2,4-dichlorophenyl)-3-{3-[(methylsulfonyl)amino]propoxy}thien-2-yl]carbonyl}-1,4'-bipiperidine-4'-carboxamide;
1'-{(4-(4-chlorophenyl)-5-(2,4-dichlorophenyl)-3-[3-(methylsulfonyl)propoxy]thien-2-yl}carbonyl)-1,4'-bipiperidine-4'-carboxamide;
1-{[4-(4-chlorophenyl)-5-(2,4-dichlorophenyl)-3-(3-hydroxypropoxy)thien-2-yl]carbonyl}-4-phenylpiperidine-4-carboxamide;
1-({4-(4-chlorophenyl)-5-(2,4-dichlorophenyl)-3-[3-(methylsulfonyl)propoxy]thien-2-yl}carbonyl)-4-phenylpiperidine-4-carboxamide;
1-{[4-(4-chlorophenyl)-5-(2,4-dichlorophenyl)-3-(2-hydroxyethoxy)thien-2-yl]carbonyl}-4-phenylpiperidine-4-carboxamide;
1'-{[4-(4-chlorophenyl)-5-(2,4-dichlorophenyl)-3-(2-hydroxyethoxy)thien-2-yl]carbonyl}-4,4-difluoro-1,4'-bipiperidine-4'-carboxamide;
1'-{[4-(4-chlorophenyl)-5-(2,4-dichlorophenyl)-3-(3-hydroxypropoxy)thien-2-yl]carbonyl}-4,4-difluoro-1,4'-bipiperidine-4'-carboxamide;
1-{[4-(4-chlorophenyl)-5-(2,4-dichlorophenyl)-3-(2-hydroxyethoxy)thien-2-yl]carbonyl}-4-[(3,3,3-trifluoropropyl)amino]piperidine-4-carboxamide;
1-({4-(4-chlorophenyl)-5-(2,4-dichlorophenyl)-3-[3-(methylsulfonyl)propoxy]thien-2-yl}carbonyl)-4-[(3,3,3-trifluoropropyl)amino]piperidine-4-carboxamide;
1-{[4-(4-chlorophenyl)-5-(2,4-dichlorophenyl)-3-{2-(hydroxyacetyl)amino]ethoxy}thien-2-yl]carbonyl}-4-[(3,3,3-trifluoropropyl)amino]piperidine-4-carboxamide;
1-{[4-(4-chlorophenyl)-5-(2,4-dichlorophenyl)-3-(3-hydroxypropoxy)thien-2-yl]carbonyl}-4-[(3,3,3-trifluoropropyl)amino]piperidine-4-carboxamide;
1-{[4-(4-chlorophenyl)-5-(2,4-dichlorophenyl)-3-{2-[(hydroxyacetyl)amino]ethoxy}thien-2-yl]carbonyl}-3-phenylpiperidine-4-carboxamide;
1-{[3-(2-acetamidoethoxy)-4-(4-chlorophenyl)-5-(2,4-dichlorophenyl)thien-2-yl]carbonyl}-4-phenylpiperidine-4-carboxamide;
1-{[4-(4-chlorophenyl)-5-(2,4-dichlorophenyl)-3-(2-hydroxyethoxy)thien-2-yl]carbonyl}-4-[(4-fluorobenzyl)amino]piperidine-4-carboxamide;
1-{[4-(4-chlorophenyl)-5-(2,4-dichlorophenyl)-3-(3-hydroxypropoxy)thien-2-yl]carbonyl}-4-[(4-fluorobenzyl)amino]piperidine-4-carboxamide;
1-{4-(4-chlorophenyl)-5-(2,4-dichlorophenyl)-3-[3-(methylsulfonyl)propoxy]thien-2-yl}carbonyl)-4-[(4-fluorobenzyl)amino]piperidine-4-carboxamide;
1-{[3-(2-acetamidoethoxy)-4-(4-chlorophenyl)-5-(2,4-dichlorophenyl)thien-2-yl]carbonyl}-4-[(4-fluorobenzyl)amino]piperidine-4-carboxamide;
1-{[4-(4-chlorophenyl)-5-(2,4-dichlorophenyl)-3-{2-[(hydroxyacetyl)amino]ethoxy}thien-2-yl]carbonyl}-4-[(4-fluorobenzyl)amino]piperidine-4-carboxamide;
1-{[4-(4-chlorophenyl)-5-(2,4-dichlorophenyl)-3-{3-[(hydroxyacetyl)amino]propoxy}thien-2-yl]carbonyl}-4-[(4-fluorobenzyl)amino]piperidine-4-carboxamide;
1-{[3-(3-acetamidopropoxy)-4-(4-chlorophenyl)-5-(2,4-dichlorophenyl)thien-2-yl]carbonyl}-4-[(4-fluorobenzyl)amino]piperidine-4-carboxamide;
4-(benzylamino)-1-{[4-(4-chlorophenyl)-5-(2,4-dichlorophenyl)-3-(2-hydroxyethoxy)thien-2-yl]carbonyl}piperidine-4-carboxamide;
4-(benzylamino)-1-{[4-(4-chlorophenyl)-5-(2,4-dichlorophenyl)-3-{2-[(hydroxyacetyl)amino]ethoxy}thien-2-yl]carbonyl}piperidine-4-carboxamide;
1-{[5-(2-chlorophenyl)-4-(4-chlorophenyl)-3-(3-hydroxypropoxy)thien-2-yl]carbonyl}-4-[(4-fluorobenzyl)amino]piperidine-4-carboxamide;
1-{[5-(2-chlorophenyl)-4-(4-chlorophenyl)-3-(3-hydroxypropoxy)thien-2-yl]carbonyl}-4-phenylpiperidine-4-carboxamide;
1-{[5-(2-chlorophenyl)-4-(4-chlorophenyl)-3-(2-hydroxyethoxy)thien-2-yl]carbonyl}-4-phenylpiperidine-4-carboxamide;
1-{[5-(2-chlorophenyl)-4-(4-chlorophenyl)-3-(2-hydroxyethoxy)thien-2-yl]carbonyl}-4-[(4-fluorobenzyl)amino]piperidine-4-carboxamide;
1-{[3-(2-aminoethoxy)-5-(2-chlorophenyl)-4-(4-chlorophenyl)thien-2-yl]carbonyl}-4-[(4-fluorobenzyl)amino]piperidine-4-carboxamide;
1-{[3-(2-acetamidoethoxy)-5-(2-chlorophenyl)-4-(4-chlorophenyl)thien-2-yl]carbonyl}-4-[(4-fluorobenzyl)amino]piperidine-4-carboxamide;
1-{[3-(2-aminoethoxy)-5-(2-chlorophenyl)-4-(4-chlorophenyl)thien-2-yl]carbonyl}-4-phenylpiperidine-4-carboxamide;
1-{[5-(2-chlorophenyl)-4-(4-chlorophenyl)-3-{2-[(hydroxyacetyl)amino]ethoxy}thien-2-yl]carbonyl}-4-phenylpiperidine-4-carboxamide;
1-{[3-(2-acetamidoethoxy)-5-(2-chlorophenyl)-4-(4-chlorophenyl)thien-2-yl]carbonyl}-4-phenylpiperidine-4-carboxamide;
1-{[5-(2-chlorophenyl)-4-(4-chlorophenyl)-3-{2-(hydroxyacetyl)amino]ethoxy}thien-2-yl]carbonyl}-4-[(4-fluorobenzyl)amino]piperidine-4-carboxamide;

in the form of a base or of an addition salt with an acid.

5. A process for preparing the compound of claim 1, comprising reacting a compound of formula:

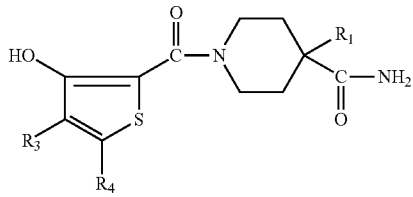 (II)

in which $R_1$, $R_3$ and $R_4$ are as defined in claim 1, in the presence of a base, with a compound of formula:

Z—R$_2$ (III)

in which $R_2$ is as defined in claim 1 and Z represents a leaving group.

6. A process for preparing the compound of claim 1, comprising reacting an acid or a functional derivative of this acid of formula:

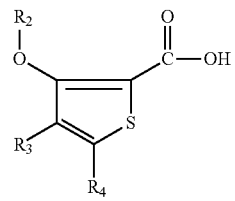 (IV)

in which $R_2$, $R_3$ and $R_4$ are as defined in claim 1, with a compound of formula:

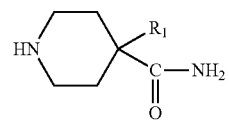 (V)

in which $R_1$ is as defined in claim 1.

7. A pharmaceutical composition comprising the compound of claim 1, or an addition salt of said compound with a pharmaceutically acceptable acid.

8. The pharmaceutical composition of claim 7, further comprising, at least one pharmaceutically acceptable excipient.

* * * * *

UNITED STATES PATENT AND TRADEMARK OFFICE
CERTIFICATE OF CORRECTION

PATENT NO. : 8,486,971 B2  Page 1 of 1
APPLICATION NO. : 13/258933
DATED : July 16, 2013
INVENTOR(S) : Ducoux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this
Eighth Day of September, 2015

Michelle K. Lee
*Director of the United States Patent and Trademark Office*